US012767732B2

(12) United States Patent
Jung et al.

(10) Patent No.: US 12,767,732 B2
(45) Date of Patent: Oct. 20, 2026

(54) BISPECIFIC ANTIBODY OR ANTIGEN-BINDING FRAGMENT THEREOF, AND PREPARATION METHOD THEREFOR

(71) Applicant: MUSTBIO CO., LTD., Gyeonggi-do (KR)

(72) Inventors: Sung Youb Jung, Seoul (KR); Young Jin Park, Gyeonggi-do (KR); Hyo Joo Bang, Gyeonggi-do (KR); Maeng Sup Kim, Seoul (KR)

(73) Assignee: MUSTBIO CO., LTD., Gyeonggi-Do (KR)

( * ) Notice: Subject to any disclaimer, the term of this patent is extended or adjusted under 35 U.S.C. 154(b) by 955 days.

(21) Appl. No.: 17/922,265

(22) PCT Filed: May 28, 2021

(86) PCT No.: PCT/KR2021/006643

§ 371 (c)(1),
(2) Date: Oct. 28, 2022

(87) PCT Pub. No.: WO2021/246720

PCT Pub. Date: Dec. 9, 2021

(65) Prior Publication Data

US 2023/0212320 A1 Jul. 6, 2023

(30) Foreign Application Priority Data

Jun. 1, 2020 (KR) ........................ 10-2020-0066030

(51) Int. Cl.
*C07K 16/46* (2006.01)
*A61K 39/00* (2006.01)
*A61P 35/00* (2006.01)
*C12N 15/63* (2006.01)

(52) U.S. Cl.
CPC ............ *C07K 16/468* (2013.01); *A61K 39/00* (2013.01); *A61P 35/00* (2018.01); *C12N 15/63* (2013.01); *C07K 2317/31* (2013.01); *C07K 2317/526* (2013.01)

(58) Field of Classification Search
CPC .............. C07K 16/468; C07K 2317/31; C07K 2317/526; C07K 2317/55; C07K 16/2809; C07K 16/2827; C07K 2319/30; C07K 2317/622; C07K 16/46; A61K 39/00; A61K 2039/505; A61P 35/00; A61P 25/28; C12N 15/63
See application file for complete search history.

(56) References Cited

U.S. PATENT DOCUMENTS 5,731,168 A 3/1998 Carter et al.
9,562,109 B2 * 2/2017 Von Kreudenstein .. A61P 37/06
10,538,595 B2 1/2020 Zhang
11,078,249 B2 8/2021 Kim et al.
2015/0038682 A1 2/2015 Tsurushita et al.
2016/0207995 A1 7/2016 Yansura et al.
2019/0031785 A1 1/2019 Schuetz et al.
2019/0352421 A1 11/2019 Adams
2022/0040297 A1 2/2022 Igawa et al.
2022/0064315 A1 3/2022 Lazar et al.
2022/0162342 A1 5/2022 Kim et al.

FOREIGN PATENT DOCUMENTS

EP 2610268 A1 7/2013
EP 3 489 262 A1 5/2019
JP 2019530434 A 10/2019
KR 1020140067944 A 6/2014
KR 1020150139905 A 12/2015
KR 1020160083094 A 11/2016
KR 1020170142996 A 12/2017
KR 102098919 B1 4/2020
RU 2604490 C2 12/2016
WO 2012058768 A1 5/2012
WO 2013166594 A1 11/2013
WO 2015017822 A1 2/2015
WO 2018027204 A1 2/2018
WO 2018030806 A1 2/2018
WO WO 2019/077092 A1 4/2019
WO WO 2019/086362 A1 5/2019
WO 2019220368 A1 11/2019

OTHER PUBLICATIONS

Byers, T. CA Cancer Journal for Clinicians, vol. 49, No. 6, Nov.-Dec. 1999 (Year: 1999).*
Choi, H.-J. et al. A heterodimeric Fe-based bispecific antibody simultaneously targeting VEGFR-2 and Met exhibits potent antitumor activity. Molecular Cancer Therapeutics. 2013, vol. 12, No. 12, pp. 2748-2759.
International Search Report (English translation) for Application No. PCT/KR2021/006643 dated Sep. 6, 2021.
Ha, J.-H. et al. Immunoglobulin Fe heterodimer platform technology : from design to applications in therapeutic antibodies and proteins. Frontiers in Immunology. 2016, vol. 7, thesis No. 394 (pp. 1-16).
Notice of Allowance for Application No. KR 21-69537 dated Feb. 4, 2022 (no translation).

(Continued)

*Primary Examiner* — Sean E Aeder
*Assistant Examiner* — Yie Chia Lee
(74) *Attorney, Agent, or Firm* — Farber LLC

(57) ABSTRACT

Provided are a protein complex having a high heterodimer formation rate, a method of preparing the same, a pharmaceutical composition for preventing or treating cancer including the protein complex, and a method or preventing or treating cancer using the same. According to the same, bispecific antibodies or antigen-binding fragments with increased stability, receptors and receptor-binding agonists, antagonists, ligands, cytokines or receptor decoy biconjugates may be easily prepared and used in various fields such as disease prevention or treatment, and disease diagnosis.

8 Claims, 15 Drawing Sheets

Specification includes a Sequence Listing.

(56) References Cited

OTHER PUBLICATIONS

Notice of Allowance for Application No. KR 22-20210 dated May 25, 2022 (no translation).
Office Action dated Oct. 24, 2023, for Japanese Patent Application No. 2023-515550 (with English translation).
Liu, Hongyan et al, Fc Engineering for Developiong Therapeutic Bispecific Antibodies and Novel Scaffolds, Frontiers in Immunology, Jan. 26, 2017, vol. 8, Article 38 (pp. 1-15), doi: 10.3389/fimmu.2017.00038.
Extended European Search Report; Application No./Patent No. 21818345.7-1111 / 4159765 PCT/KR2021006643; Mustbio Co., Ltd; Jul. 9, 2024.
Search Report dated Jul. 5, 2023 for Russian Application #2022127374/10.
Office Action dated Jul. 5, 2023 for Russian Application #2022127374/10.
Choi H.J. et al., Engineering of Immunoglobulin Fc Heterodimers Using Yeast Surface-Displayed Combinatorial Fc Library Screening, PLoS One, 2015, vol. 10, N. 12, e0145349, see Table 1, variant A109, the paragraph on p. 8-9, Fig. 3b.
Xu Y. et al., Production of bispecific antibodies in "knobs-into-holes" using a cell-free expression system, MAbs, 2015, vol. 7 N. 1, pp. 231-242, the abstract.
Moore G.L. et al., A robust heterodimeric Fc platform engineered for efficient development of bispecific antibodies of multiple formats, Methods, 2019, vol. 154, pp. 38-50, the abstract.

* cited by examiner

Data were analyzed using Welch's ANOVA followed by Dunnett's T3 test.
*P<0.05,**P<0.01 compared with the Vehicle group.
#P<0.05 compared with the Avelumab group.

BISPECIFIC ANTIBODY OR ANTIGEN-BINDING FRAGMENT THEREOF, AND PREPARATION METHOD THEREFOR

FIELD OF THE INVENTION

The present disclosure relates to a bispecific antibody having a high heterodimer formation rate, or an antigen-binding fragment thereof, and a method of preparing the same.

BACKGROUND OF THE INVENTION

Natural human immunoglobulin (Ig) consists of two identical heavy chains and two light chains joined together. In addition, immunoglobulins may be functionally divided into an antigen-binding fragment (Fab) region that forms antigen-antibody binding and a fragment crystallizable (Fc) region in which two heavy chains form a dimer. These natural immunoglobulins, i.e., monoclonal antibodies (mAbs), generally target the same binding site (epitope) of the same antigen because the two Fab regions are identical to each other, and have bi-valent and mono-specific binding properties.

Immunoglobulins are widely used as a therapeutic agent for various diseases due to a target-specific antigen-binding function of the Fab region and a function of the Fc region of inducing immune cells and increasing in vivo half-life. However, recently, in intractable diseases such as cancer or autoimmune diseases, a synergistic treatment using two drugs acting on different targets has shown a greater therapeutic effect than using a single drug, and as a result, various bispecific antibodies that may act on two target substances are being developed.

Among the bispecific antibodies being developed thus, scFv-scFv type bispecific antibodies, in which variable region fragments of different antibodies are linked with a polypeptide chain, have the disadvantage of not being able to stay in the body for a long time and to sustain efficacy due to their small molecular weight and low stability. In addition, scFv-Fab-Fc or Fab-Fc-scFv type bispecific antibodies, in which an end of a natural immunoglobulin polypeptide is linked to a variable region fragment of another antibody, have disadvantages of having the potential to form an aggregate due to the low structural stability, and to show immunogenicity in vivo. Therefore, in order to solve these issues, it is necessary to develop bispecific antibodies having different variable regions while following the form of a natural immunoglobulin as much as possible.

In order to form this type of bispecific antibody, a heterodimer must be formed between the Fc regions of two different Fab-Fc complexes. Since the amino acids at positions where CH3 domains interact with each other play an important role in Fc heterodimer formation, Fc heterodimer technology is being developed in such a way that these amino acids are substituted with other amino acids. (U.S. Pat. No. 5,731,168 A (1998.03.24), Korean patent No. 10-2098919 (2020.04.02)).

However, the existing Fc heterodimer technology developed in this way also has the limitation of not being able to make all Fc structures in the form of 100% heterodimers, and forms a mixture of heterodimers and homodimers.

Therefore, there is a need to develop a protein complex with improved heterodimer formation efficiency, a bispecific antibody including the same or an antigen-binding fragment thereof, receptors and receptor-binding agonists, antagonists, ligands, receptor decoy biconjugates, and the like.

SUMMARY OF THE INVENTION

Technical Problem

An aspect is to provide a protein complex having a high heterodimer formation rate.

Another aspect is to provide a method of preparing the protein complex having a high heterodimer formation rate.

Still another aspect is to provide a pharmaceutical composition for preventing or treating a disease including the protein complex having a high heterodimer formation rate.

Still another aspect is to provide a method of preventing or treating a disease using the protein complex having a high heterodimer formation rate.

Still another aspect is to provide uses of the protein complex having a high heterodimer formation rate for preparation of a preventive or therapeutic agent for a disease.

Solution to Problem

An aspect provides a protein complex including a first polypeptide including a first CH3 antibody constant region and a second polypeptide including a second CH3 antibody constant region, wherein the first polypeptide and the second polypeptide form a heterodimer.

In an embodiment, the first CH3 antibody constant region includes a tryptophan (W) at position 366, and the second CH3 antibody constant region includes a serine (S) at position 366, an alanine (A) at position 368, and a valine (V) at position 407; and at least one of the first CH3 antibody constant region and the second CH3 antibody constant region may include at least one amino acid selected from the group consisting of phenylalanine (F), tryptophan (W), histidine (H), glycine (G), valine (V), methionine (M) and alanine (A), at one or more positions selected from the group consisting of positions 351 and 394.

The protein complex includes a first polypeptide including a first CH3 antibody constant region and a second polypeptide including a second CH3 antibody constant region, wherein the first polypeptide and the second polypeptide form a heterodimer.

The term "antibody" is used interchangeably with the term "immunoglobulin (Ig)". A complete antibody has a structure having two full-length light chains and two full-length heavy chains, and each light chain is bound to a heavy chain by a disulfide bond (SS-bond). The light chain has two types, λ and κ, and consists of approximately 211 to 217 amino acids. There is only one kind of a light chain in each human antibody. The light chain consists of a constant region and a variable region continuously connected. The heavy chain has five (γ, δ, α, μ, ε) types, and the heavy chain determines the type of an antibody. α and γ consist of 450 amino acids, and μ and ε consist of 550 amino acids. The heavy chain has two regions, a variable region and a constant region. The variable region refers to a region to which an antigen binds in an antibody. The variable region may include a complementarity determining region (CDR) conferring antigen-binding specificity.

The antibody may include an antigen-binding fragment (Fab) region that binds to an antigen and a fragment crystallizable (Fc) region that binds to a cell surface receptor. When cleaved with papain, the complete antibody may be cleaved into two Fab regions and one Fc region. The Fab region may be one, in which a polypeptide including a heavy chain variable region (VH) domain and a heavy chain constant region 1 (CH1) domain, and a polypeptide including a light chain variable region (VL) domain and a light chain constant region (CL) domain, are linked by a disulfide bond. The Fc region may be one in which two polypeptides including a heavy chain constant region 2 (CH2) domain and a constant region 3 (CH3) domain are linked. The Fc region may form a hinge region.

The CH3 antibody constant region refers to the heavy chain constant region 3 domain of an antibody.

A first polypeptide and a second polypeptide may form a Fc region of an antibody.

The heterodimer refers to a combination of two polypeptides having different sequences, numbers, or types of amino acid residues. The protein complex may be a bispecific antibody or an antigen-binding fragment thereof formed by combining of two polypeptides that specifically bind to targets different from each other.

The protein complex may be a bispecific antibody or an antigen-binding fragment thereof, a conjugate of a receptor and an agonist, a conjugate of a receptor and an antagonist, a conjugate of a receptor and a ligand, or a conjugate of a ligand and a decoy receptor. In addition, the protein complex may include any one selected from the group consisting of an antigen-binding fragment (Fab), a single chain variable fragment (scFv), an extracellular domain of a membrane receptor, an agonist, an antagonist, a ligand, a decoy receptor, a cytokine, a coagulation factor, and an affinity tag.

The antibody may be, for example, IgA, IgD, IgE, IgG, or IgM. The antibody may be a monoclonal antibody or a polyclonal antibody. The antibody may be an animal-derived antibody, a mouse-human chimeric antibody, a humanized antibody, or a human antibody.

The term "antigen-binding fragment" refers to a fragment of an entire immunoglobulin structure, and refers to a portion of a polypeptide including a part capable of binding to an antigen. For example, an antigen binding fragment may be scFv, $(scFv)_2$, Fv, Fab, Fab', Fv $F(ab')_2$, or a combination thereof.

The term "bispecific" refers to specific recognition of target proteins different from each other. A bispecific antibody or an antigen-binding fragment thereof refers to an antibody or an antigen-binding fragment thereof having two antigen-binding sites that recognize different target antigens. A bispecific antibody or an antigen-binding fragment thereof may also be referred to as a bispecific antibody (BsAb).

The bispecific antibody or antigen-binding fragment thereof may be a knob into hole (kih) IgG, scFv-Fc, scFv2-Fc, TrioMab, IgG-like antibody, CrossMab, 2:1 CrossMab, 2:2 CrossMab, DuoBody, DVD-Ig (dual variable domain immunoglobulin), scFv-IgG, IgG-IgG, Fab-scFv-Fc, ADP-TIR, BiTE (bispecific T cell engager)-Fc, DART (Dual affinity retargeting)-Fc, Tetravalent DART-Fc, LP-DART, CODV (cross-over dual variable)-Ig, CODV-Fab-TL, HLE (half-life extended)-Bite, Tandem $V_{HH}$ (heavy chain-only variable domain)-Fc, or a combination thereof.

The term "receptor" refers to a substance that receives or transmits a signal that may be transmitted to a biological system. The receptor may be a protein receptor. The receptor may bind to an agonist, an antagonist, a ligand, or a cytokine. The agonist may be a substance that binds to a receptor and activates the receptor to induce a biological response. The antagonist may be a substance that binds to a receptor and inhibits the receptor to inhibit a biological response. The ligand may be a substance that binds to a receptor. The ligand may bind to a decoy receptor. The decoy receptor refers to a receptor that specifically binds to a ligand, thereby inhibiting signal transduction by an actual receptor. The cytokine refers to a small protein that acts on cell signaling, and regulation and maintenance of inflammatory processes.

The protein complex may be modified. For example, the protein complex may be modified by conjugation or binding, glycosylation, tag attachment, or a combination thereof. The antibody may be conjugated with other drugs such as anticancer drugs. For example, the protein complex may be one combined with a horseradish peroxidase (HRP), an alkaline phosphatase, hapten, biotin, streptavidin, a fluorescent material, a radioactive material, quantum dots, polyethylene glycol (PEG), a histidine tag, or a combination thereof. The fluorescent material may be Alexa Fluor® 532, Alexa Fluor® 546, Alexa Fluor®568, Alexa Fluor® 680, Alexa Fluor®750, Alexa Fluor®790, or Alexa Fluor®350.

The position of the amino acid is according to the Kabat EU index (EU-index as described in 'Kabat et al., Sequences of Proteins of Immunological Interest, 5th Ed. Public Health Service, National Institutes of Health, Bethesda, MD (1991)'). The position of the amino acid of the CH3 domain and the corresponding amino acid type are based on human IgG1.

In the protein complex, the first CH3 antibody constant region may include a tryptophan (W) at position 366. In the first CH3 antibody constant region, position 366 may be one (T366W) in which threonine (T) is substituted with tryptophan (W). The second CH3 antibody constant region may include serine (S) at position 366, alanine (A) at position 368, and valine (V) at position 407. In the second CH3 antibody constant region, position 366 may be one (T366S) in which threonine (T) is substituted with serine (S). In the second CH3 antibody constant region, position 368 may be one (L368A) in which leucine (L) is substituted with alanine (A). In the second CH3 antibody constant region, the position 407 may be one (Y407V) in which tyrosine (Y) is substituted with valine (V).

In the protein complex, at least one of the first CH3 antibody constant region and the second CH3 antibody constant region may include at least one amino acid selected from the group consisting of phenylalanine (F), tryptophan (W), histidine (H), glycine (G), valine (V), methionine (M), alanine (A), isoleucine (1), and serine (S), at one or more positions selected from the group consisting of positions 351 and 394.

For example, the first CH3 antibody constant region may include at least one amino acid selected from the group consisting of phenylalanine (F), tryptophan (W), histidine (H), glycine (G), valine (V), methionine (M), alanine (A), and isoleucine (1), at one or more positions selected from the group consisting of positions 351 and 394. In addition, the second CH3 antibody constant region may include at least one amino acid selected from the group consisting of phenylalanine (F), tryptophan (W), histidine (H), glycine (G), valine (V), methionine (M), alanine (A), and serine (S), at one or more positions selected from the group consisting of positions 351 and 394.

In an embodiment, the first CH3 antibody constant region may include tryptophan (W) at position 366, and phenylalanine (F), histidine (H), or tryptophan (W) at position 394. The position 394 may be one in which threonine (T) is substituted with phenylalanine (F), histidine (H), or tryptophan (W) (T394F, T394H, or T394W).

In another embodiment, the first CH3 antibody constant region may include tryptophan (W) at position 366, and may include tryptophan (W), valine (V), alanine (A), or phenylalanine (F) at position 351. The position 351 may be one in which leucine (L) is substituted with tryptophan (W), valine (V), alanine (A), or phenylalanine (F) (L351W, L351V, L351A, or L351F).

In another embodiment, the second CH3 antibody constant region may include serine (S) at position 366, alanine (A) at position 368, valine (V) at position 407, and alanine (A), glycine (G), valine (V), methionine (M) or phenylalanine (F) at position 351. The position 351 may be one in which leucine (L) is substituted with alanine (A), glycine (G), valine (V), methionine (M), or phenylalanine (F) (L351A, L351G, L351V, L351M, or L351F).

The first CH3 antibody constant region may include one selected from the group consisting of:

- tryptophan (W) at position 366;
- tryptophan (W) at position 366, and histidine (H) at position 394;
- tryptophan (W) at position 366, and phenylalanine (F) at position 394;
- tryptophan (W) at position 366, and tryptophan (W) at position 394;
- tryptophan (W) at position 366, and phenylalanine (F) at position 351;
- tryptophan (W) at position 366, and tryptophan (W) at position 351;
- tryptophan (W) at position 366, and valine (V) at position 351;
- tryptophan (W) at position 366, and alanine (A) at position 351; and
- tryptophan (W) at position 366, histidine at position 394 (H), and phenylalanine at position 351 (F).

The second CH3 antibody constant region may include one selected from the group consisting of:

- serine (S) at position 366, alanine (A) at position 368, and valine (V) at position 407;
- serine (S) at position 366, alanine (A) at position 368, valine (V) at position 407, and alanine (A) at position 351;
- serine (S) at position 366, alanine (A) at position 368, valine (V) at position 407, and glycine (G) at position 351;
- serine (S) at position 366, alanine (A) at position 368, valine (V) at position 407, and valine (V) at position 351;
- serine (S) at position 366, alanine (A) at position 368, valine (V) at position 407, and methionine (M) at position 351; and
- serine (S) at position 366, alanine (A) at position 368, valine (V) at position 407, and phenylalanine (F) at position 351.

The first CH3 antibody constant region may include tryptophan (W) at position 366 and phenylalanine (F), histidine (H), or tryptophan (W) at position 394; and the second CH3 antibody constant region may include serine (S) at position 366, alanine (A) at position 368, and valine (V) at position 407.

The first CH3 antibody constant region may include tryptophan (W) at position 366 and phenylalanine (F) at position 351; and the second CH3 antibody constant region may include serine (S) at position 366, alanine (A) at position 368, valine (V) at position 407, and alanine (A) at position 351. The first CH3 antibody constant region may further include histidine (H) at position 394.

The first CH3 antibody constant region may include tryptophan (W) at position 366; and the second CH3 antibody constant region may include serine (S) at position 366, alanine (A) at position 368, valine (V) at position 407, and glycine (G) at position 351. The first CH3 antibody constant region may further include phenylalanine (F), or tryptophan (W) at position 351.

The first CH3 antibody constant region may include tryptophan (W) at position 366; and the second CH3 antibody constant region may include serine (S) at position 366, alanine (A) at position 368, valine (V) at position 407, and alanine (A), phenylalanine (F), valine (V), or methionine (M) at position 351. The first CH3 antibody constant region may further include valine (V) or alanine (A) at position 351. For example, the first CH3 antibody constant region may include tryptophan (W) at position 366 and valine (V) at position 351; and the second CH3 antibody constant region may include serine (S) at position 366, alanine (A) at position 368, valine (V) at position 407, and alanine (A) at position 351. In addition, the first CH3 antibody constant region may include tryptophan (W) at position 366 and alanine (A) at position 351; and the second CH3 antibody constant region may include serine (S) at position 366, alanine (A) at position 368, valine (V) at position 407, and phenylalanine (F) at position 351.

The protein complex according to an aspect may be a variant of the Fc variant substituted with a reverse sequence. The term "reverse sequence substitution variant", used herein, refers to a structure, in which the left and right heavy chain constant regions of a protein complex are symmetrical with respect to the Y-axis on the coordinate plane. For example, the reverse sequence substitution variant has the same specific position and type of amino acid substitution in the protein complex according to an embodiment, but the first CH3 antibody constant region and the second CH3 antibody constant region may have a structure symmetrical with respect to the Y-axis on the coordinate plane. Since the reverse sequence substitution variant forms a heterodimer in a rate similar to that before a specific amino acid is substituted, it is possible to form an Fc variant with high efficiency. Specific details regarding the protein complex are as described above.

In an embodiment, the first CH3 antibody constant region may include serine (S) at position 366, alanine (A) at position 368, and valine (V) at position 407; and the second CH3 antibody constant region may include tryptophan (W) at position 366; and at least one of the first CH3 antibody constant region and the second CH3 antibody constant region may include at least one amino acid selected from the group consisting of phenylalanine (F), tryptophan (W), histidine (H), glycine (G), valine (V), methionine (M), and alanine (A), at one or more positions selected from the group consisting of positions 351 and 394. Specific details regarding the first CH3 antibody constant region and the second CH3 antibody constant region are as described above.

In addition, the first CH3 antibody constant region may include serine (S) at position 366, alanine (A) at position 368, valine (V) at position 407, and glycine (G) at position 351; and the second CH3 antibody constant region may include tryptophan (W) at position 366. The second CH3 antibody constant region may further include phenylalanine (F) or tryptophan (W) at position 351.

In an embodiment, as a result of comparing the heterodimer formation rate of wild-type IgG1 and Genentech's knobs-into-hole (KiH) bispecific antibody with that of Fc variants selected after substituting amino acids at specific positions in the CH3 antibody constant region of the antibody, it was confirmed that the heterodimer formation rate of the Fc variants was noticeably higher, and the thermodynamic stability was also excellent. In addition, it was confirmed that the heterodimer formation rate was also noticeably higher in variants of the Fc variants substituted with a reverse sequence, compared to the wild-type IgG1 and Genentech's knobs-into-hole (KiH) bispecific antibody. Therefore, the protein complex according to an aspect has improved heterodimer formation efficiency, and thus, the protein complex may be used as a bispecific antibody including the same or an antigen-binding fragment thereof, a receptor and a receptor-binding agonist, an antagonist, a ligand, a cytokine, and a receptor decoy biconjugate, and the like.

Another aspect provides a method of preparing a protein complex including: transforming one or more cells with one or more expression vectors encoding the first polypeptide according to an aspect, the second polypeptide according to an aspect, or a combination thereof; and expressing the first polypeptide, the second polypeptide, or a combination thereof.

Specific details regarding the first polypeptide, the second polypeptide, and the protein complex are as described above.

"Expression vector" refers to an expression vector capable of expressing a target protein in appropriate host cells, and refers to a vector including essential regulatory elements operably linked so that an inserted nucleic acid sequence may be expressed. The "operably linked" means that the nucleic acid expression regulatory sequence and the nucleic acid encoding the target protein are functionally linked to perform a general function. The expression vector may include a polynucleotide encoding the first polypeptide, the second polypeptide, or a combination thereof. The expression vector may include a regulatory region necessary for gene expression, for example, an enhancer, a promoter, a poly(A) sequence, and the like.

The cells may be cancer cells. The cells may be in vitro cells. The cells may be bacteria, yeasts, plant cells, or mammalian cells. The bacteria may be *E. coli*. The mammalian cells refer to cells derived from mice, rats, rabbits, dogs, cats, sheep, cows, horses, monkeys, chimpanzees, or humans. The cells may be a cell line. The cells may be, for example, selected from the group consisting of Chinese hamster ovary (CHO) cells, human embryonic kidney (HEK) cells, baby hamster kidney (BHK) cells, NS0 cells, PER.C6 cells, HeLa cells, Madin-Darby Canine Kidney (MDCK) cells, SP2/0 mouse myeloma cells, COS-7, and YB2/0 rat myeloma cells. The CHO cells may be CHO DG44, CHO-K1, CHO-S, GS-CHO, or CHO DUKX (DXB11) cells. The HEK cells may be HEK 293 cells.

"Transformation" refers to a method of inserting a specific nucleic acid fragment into the genome of a cell so that the inserted nucleic acid is expressed.

An expression vector encoding the first polypeptide and an expression vector encoding the second polypeptide may be co-transfected into cells, or an expression vector encoding the first polypeptide and an expression vector encoding the second polypeptide may be transformed into at least two types of cells, with a vector for each cell type.

The cells may be cultured in a cell culture medium. The cell culture medium refers to a solution containing nutrients necessary for culturing cells. The medium includes a commercialized or prepared medium used for culturing cells. The cell culture medium may contain an antibiotic. The cell culture medium may include G418 (geneticin), puromycin, blasticidin, zeocin, or a combination thereof. The cell culture medium may include a chemically defined medium.

The cells may be cultured under conditions that allow for survival or proliferation of the cells. Conditions allowing survival or proliferation of the cells may vary depending on the type of the cells. The cells may be cultured at about 25° C. to about 42° C., about 25° C. to about 40° C., about 30° C. to about 40° C., about 30° C. to about 37° C., or about 37° C. The cells may be cultured in the presence of air having about 1% $CO_2$ to about 10% $CO_2$, or about 5% $CO_2$ to about 10% $CO_2$. The cells may be cultured in a medium of about pH 6 to about pH 8, about pH 6.2 to about pH 7.8, about pH 6.4 to about pH 7.6, about pH 6.6 to about pH 7.4, or about pH 6.8 to about pH 7.2. The cells may be cultured in a condition of dissolved oxygen of about 10% to about 80%, about 15% to about 70%, or about 20% to about 60%.

The culture may vary depending on the type of the cells. The culture may use a known method. The culture may be performed on a plate, flask, or the like. The culture may be performed by attaching the cells to a substrate or floating the cells in a culture medium. The culture may be a subculture, a batch culture, a fed-batch culture, a perfusion culture, or a combination thereof. During the culture, the cell culture medium may be periodically exchanged with a fresh medium. The cells may be cultured for about 1 day or more, about 2 days or more, about 3 days or more, about 4 days or more, about 5 days or more, about 6 days or more, about 1 week or more, about 10 days or more, about 2 weeks or more, about 3 weeks or more, about 1 month or more, from about 1 day to about 1 month, about 1 day to about 3 weeks, about 1 day to about 2 weeks, about 2 days to about 2 weeks, about 3 days to about 2 weeks, about 4 days to about 2 weeks, about 5 days to about 2 weeks, about 6 days to about 2 weeks, or about 1 week to about 2 weeks.

Obtaining a protein complex of the first polypeptide, the second polypeptide, or the first polypeptide and the second polypeptide from the cells or the cell culture medium may be included.

The cell culture medium may be a culture medium without the cells.

When the expression vector is co-transformed into cells, a protein complex of the first polypeptide and the second polypeptide may be obtained from the cells or the cell culture medium. When at least two types of cells are transformed with the expression vector encoding the first polypeptide and the expression vector encoding the second polypeptide, with a vector for each cell type, the first polypeptide and the second polypeptide may be obtained from the cells or cell culture mediums.

Obtaining the protein complex may include incubating the obtained first polypeptide and the obtained second polypeptide to form a protein complex. The incubation may be performed under a reducing condition. The reducing condition may be in the presence of 2-mercaptoethanol (2-ME), dithiothreitol (DTT), or a combination thereof.

Obtaining the protein complex may include purifying the protein complex. The purification may be performed by filtration, centrifugation, chromatography, dialysis, immunoprecipitation, or a combination thereof.

Another aspect provides a pharmaceutical composition for preventing or treating cancer including the protein complex according to an aspect.

Specific details regarding the protein complex are as described above.

The cancer may be a solid cancer or a non-solid cancer. Solid cancer refers to cancerous tumors that occurred in organs such as liver, lung, breast, skin, etc. Non-solid cancers are cancers that occurred in the blood and are also called blood cancers. The cancer may be a carcinoma, a sarcoma, a hematopoietic cell-derived cancer, a germ cell tumor, or a blastoma. The cancer may be selected from the group consisting of breast cancer, skin cancer, head and neck cancer, pancreatic cancer, lung cancer, colorectal cancer, stomach cancer, ovarian cancer, prostate cancer, bladder cancer, urethral cancer, liver cancer, kidney cancer, clear cell sarcoma, melanoma, cerebrospinal tumor, brain cancer, thymoma, mesothelioma, esophageal cancer, biliary tract cancer, testicular cancer, germ cell tumor, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, endocrine cancer, and sarcoma.

The term "prevention" refers to any action that inhibits a disease or delays the onset of a disease by administration of the pharmaceutical composition. The term "treatment" refers to any action that improves or beneficially changes the symptoms of a disease by administration of the pharmaceutical composition.

The pharmaceutical composition may include a pharmaceutically acceptable carrier. The term "carrier" is used to include excipients, diluents or adjuvants. The carrier may be, for example, selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, physiological saline, buffers such as PBS, methylhydroxy benzoate, propylhydroxy benzoate, talc, magnesium stearate, and mineral oil. The composition may include a filler, an anti-agglomeration agent, a lubricant, a wetting agent, a flavoring agent, an emulsifying agent, a preservative, or a combination thereof.

The pharmaceutical composition may be prepared in any formulation according to a method in the art. The composition may be formulated, for example, as a formulation for oral administration (for example, powder, tablet, capsule, syrup, pill, or granule), or a formulation for parenteral administration (for example, injection). In addition, the composition may be prepared as a systemic formulation, or as a local formulation.

The pharmaceutical composition may further include other anticancer agents. The anticancer agent may be cetuximab, panitumumab, erlotinib, gefitinib, trastuzumab, T-DM1, perjeta, lapatinib, paclitaxel, taxol, tamoxifen, cisplatin, or a combination thereof. The pharmaceutical composition may be a single composition or separate compositions. For example, the composition of an antibody or an antigen-binding fragment thereof may be a composition for parenteral administration, and the anticancer agent may be a composition for oral administration.

The pharmaceutical composition may include the protein complex in an effective amount. The term "effective amount" means an amount sufficient to exhibit an effect of prevention or treatment when administered to a subject in need of prevention or treatment of a disease. The effective amount may be appropriately selected by those skilled in the art depending on the cell or the subject. The effective amount may be determined based on the severity of disease, age, weight, health, sex of the patient, patient's sensitivity to the drug, time of administration, route of administration and rate of excretion, duration of treatment, drug used in combination or simultaneously with the composition used, and other factors well known in the medical field. The effective amount may be about 0.5 μg to about 2 g, about 1 μg to about 1 g, about 10 μg to about 500 mg, about 100 μg to about 100 mg, or about 1 mg to about 50 mg per the pharmaceutical composition.

The dosage of the pharmaceutical composition may be, for example, in the range of from about 0.001 mg/kg to about 100 mg/kg, from about 0.01 mg/kg to about 10 mg/kg, or from about 0.1 mg/kg to about 1 mg/kg, for an adult. The administration may be administered once a day, multiple times a day, once a week, once every 2 weeks, once every 3 weeks, or once every 4 weeks to once a year.

Another aspect provides a method of preventing or treating cancer, including administering the protein complex according to an aspect to a cell or a subject.

Specific details regarding the protein complex, cells, cancer, prevention, or treatment are as described above.

The subject may be a mammal, for example, a human, a cow, a horse, a pig, a dog, sheep, a goat, or a cat. The subject may be a subject that has cancer or is likely to have cancer.

The method may further include administering a second active ingredient to the subject. The second active ingredient may be an active ingredient for preventing or treating cancer. The active ingredient may be administered simultaneously, separately, or sequentially with the protein complex.

The protein complex may be, for example, administered directly into a subject by any means, such as, oral, intravenous, intramuscular, transdermal, mucosal, intranasal, intratracheal, or subcutaneous administration. The protein complex may be administered systemically or locally, alone or in combination with other pharmaceutically active compounds.

The effective amount of the protein complex may vary depending upon the patient's condition and body weight, severity of the disease, formulation of the drug, route and duration of administration, etc., and may be appropriately selected by those skilled in the art. The dosage may be, for example, in the range of from about 0.001 mg/kg to about 100 mg/kg, from about 0.01 mg/kg to about 10 mg/kg, or from about 0.1 mg/kg to about 1 mg/kg for an adult. For the administration, the protein complex may be administered once a day, multiple times a day, once a week, once every 2 weeks, once every 3 weeks, or once every 4 weeks to once a year.

Advantageous Effects of Disclosure

According to a protein complex having a high heterodimer formation rate, a method of preparing the same, a pharmaceutical composition for preventing or treating cancer including the protein complex, and a method of preventing or treating cancer using the same, bispecific antibodies or antigen-binding fragments with increased stability, receptors and receptor-binding agonists, antagonists, ligands, cytokines or receptor decoy biconjugates may be easily prepared and used in various fields such as disease prevention or treatment, and disease diagnosis.

DETAILED DESCRIPTION OF THE INVENTION

Mode of Disclosure

Figure 1:
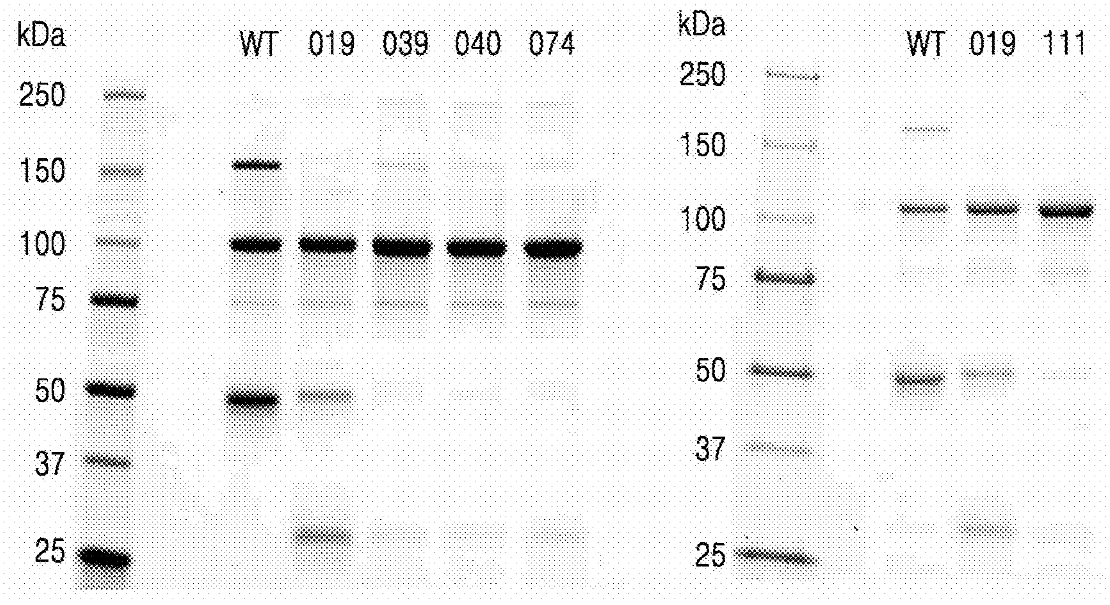
FIG. 1 is an image showing results of SDS-PAGE analysis of Fc variants (M: size marker, WT: PTCWT (negative control group), 019: PTC019 (positive control group), 039: PTC039, 040: PTC040, 074: PTC074, 111: PTC111).

Hereinafter, preferred examples are presented to help gain a better understanding of the present disclosure. However, the following examples are only provided for easier understanding of the present disclosure, and the contents of the present disclosure are not limited by the following examples.

EXAMPLES

Example 1. Preparation of Fc Heterodimer Variants

In order to evaluate Fc heterodimer-forming ability, which is changed due to amino acid substitution in a CH3 domain of an antibody, an expression system for each designed Fc variant was constructed.

In order to facilitate distinction and analysis of the two Fc polypeptides constituting a heterodimer, the first polypeptide was designed to express an IgG chain (Fc1) of an intact form, in which both the heavy chain and the light chain are linked, and the second polypeptide was designed to express only the heavy chain Fc region (Fc2). In Fc1, amino acids in a CH3 domain were substituted based on an Avelumab antibody (Bavencio®, Pfizer) including a wild-type IgG1 Fc region, and in Fc2, amino acids in the CH3 domain were substituted based on a Fc region of a wild-type IgG1 antibody. The Fc1 light chain has the same amino acid sequence as the light chain of an Avelumab antibody (SEQ ID NO: 2).

For comparison, the wild-type IgG1 (corresponding to "PTCWT" in Table 1) was used as a negative control group, and Genentech's knobs-into-hole (KiH) bispecific antibody (corresponding to "PTC019" in Table 1) was used as a positive control group.

Specifically, expression vectors were prepared by introducing a nucleotide open reading frame (ORF) encoding each polypeptide into pCHO1.0 vectors. An ExpiCHO-S™ (Thermo Fisher) cell line was cultured in ExpiCHO™ expression medium. Fc1 expression vectors and Fc2 expression vectors were mixed at a ratio of 1:1 and transfected into the ExpiCHO-S™ cell line by using an ExpiFectamie™ CHO Transfection Kit (Thermo Fisher). After culturing the transfected cells in an expression medium, the culture medium was separated and recovered. The recovered culture medium was purified by using a Protein A HP SpinTrap™ column (GE Healthcare). For the purified protein, the buffer was exchanged with PBS (pH 7.4), and the protein concentration was measured.

The expressed amino acid sequences were as described below.

[PTCWT]

Fc1 heavy chain:

(SEQ ID NO: 1)

EVQLLESGGG LVQPGGSLRL SCAASGFTFS SYIMMWWRQA PGKGLEWVSS IYPSGGITFY

ADTVKGRFTI SRDNSKNTLY LQMNSLRAED TAVYYCARIK LGTVTTVDYW GQGTLVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLGG

PSVFLFPPKP KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ VYTLPPSRDE

LTKNQVSLTC LVKGFYPSDI AVEWESNGQP ENNYKTTPPV LDSDGSFFLY SKLTVDKSRW

QQGNVFSCSV MHEALHNHYT QKSLSLSPGK (Bold: L351, bold and underlined: T366)

-continued

Fc1 light chain:

(SEQ ID NO: 2)

QSALTQPASV SGSPGQSITI SCTGTSSDVG GYNYVSWYQQ HPGKAPKLMI YDVSNRPSGV

SNRFSGSKSG NTASLTISGL QAEDEADYYC SSYTSSSTRV FGTGTKVTVL GQPKANPTVT

LFPPSSEELQ ANKATLVCLI SDFYPGAVTV AWKADGSPVK AGVETTKPSK QSNNKYAASS

YLSLTPEQWK SHRSYSCQVT HEGSTVEKTV APTECS

Fc chain of Fc2:

(SEQ ID NO: 3)

EPKSCDKTHTCPPCP APELLGGPSV FLFPPKPKDT LMISRTPEVT

CVVVDVSHED PEVKFNWYVD

GVEVHNAKTK PREEQYNSTY RVVSVLTVLH QDWLNGKEYK CKVSNKALPA

PIEKTISKAK

GQPREPQVYT LPPSRDELTK NQVSLTCLVK GFYPSDIAVE WESNGQPENN

YKTTPPVLDS

DGSFFL*Y*SKL TVDKSRWQQG NVFSCSVMHE ALHNHYTQKS LSLSPGK
(Bold: L351, bold and underlined: T366, underlined: L368, italic: Y407)

[PTC019]
Fc1 heavy chain:

(SEQ ID NO: 4)

EVQLLESGGG LVQPGGSLRL SCAASGFTFS SYIMMWVRQA PGKGLEWVSS IYPSGGITFY

ADTVKGRFTI SRDNSKNTLY LQMNSLRAED TAVYYCARIK LGTVTTVDYW GQGTLVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLGG

PSVFLFPPKP KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ VYTLPPSRDE

LTKNQVSLWC LVKGFYPSDI AVEWESNGQP ENNYKTTPPV LDSDGSFFLY SKLTVDKSRW

QQGNVFSCSV MHEALHNHYT QKSLSLSPGK
(Bold: L351, bold and underlined: T366W)

(SEQ ID NO: 2)

Fc1 light chain

Fc chain of Fc2:

(SEQ ID NO: 5)

EPKSCDKTHTCPPCP APELLGGPSV FLFPPKPKDT LMISRTPEVT

CVVVDVSHED PEVKFNWYVD

GVEVHNAKTK PREEQYNSTY RVVSVLTVLH QDWLNGKEYK CKVSNKALPA

PIEKTISKAK

GQPREPQVYT LPPSRDELTK NQVSLSCAVK GFYPSDIAVE WESNGQPENN

YKTTPPVLDS

DGSFFL*V*SKL TVDKSRWQQG NVFSCSVMHE ALHNHYTQKS LSLSPGK
(Bold: L351, bold and underlined: T366S, underlined: L368A, italic: Y407V)

[PTC039]
Fc1 heavy chain:

(SEQ ID NO: 6)

EVQLLESGGG LVQPGGSLRL SCAASGFTFS SYIMMWVRQA PGKGLEWVSS IYPSGGITFY

ADTVKGRFTI SRDNSKNTLY LQMNSLRAED TAVYYCARIK LGTVTTVDYW GQGTLVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLGG

PSVFLFPPKP KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ VYTFPPSRDE

-continued

LTKNQVSLWC LVKGFYPSDI AVEWESNGQP ENNYKTTPPV LDSDGSFFLY SKLTVDKSRW

QQGNVFSCSV MHEALHNHYT QKSLSLSPGK
(Bold: L351F, bold and underlined: T366W)

(SEQ ID NO: 2)
Fc1 light chain

Fc chain of Fc2:
(SEQ ID NO: 7)
EPKSCDKTHTCPPCP APELLGGPSV FLFPPKPKDT LMISRTPEVT

CVVVDVSHED PEVKFNWYVD

GVEVHNAKTK PREEQYNSTY RVVSVLTVLH QDWLNGKEYK CKVSNKALPA

PIEKTISKAK

GQPREPQVYT GPPSRDELTK NQVSLSCAVK GFYPSDIAVE WESNGQPENN

YKTTPPVLDS

DGSFFL*V*SKL TVDKSRWQQG NVFSCSVMHE ALHNHYTQKS LSLSPGK
(Bold: L351G, bold and underlined: T366S, underlined: L368A, italic: Y407V)

[PTC040]
Fc1 heavy chain:
(SEQ ID NO: 8)
EVQLLESGGG LVQPGGSLRL SCAASGFTFS SYIMMWVRQA PGKGLEWVSS IYPSGGITFY

ADTVKGRFTI SRDNSKNTLY LQMNSLRAED TAVYYCARIK LGTVTTVDYW GQGTLVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLGG

PSVFLFPPKP KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ VYTWPPSRDE

LTKNQVSLWC LVKGFYPSDI AVEWESNGQP ENNYKTTPPV LDSDGSFFLY SKLTVDKSRW

QQGNVFSCSV MHEALHNHYT QKSLSLSPGK
(Bold: L351W, bold and underlined: T366W)

Fc1 light chain
(SEQ ID NO: 2)

Fc chain of Fc2
(SEQ ID NO: 7)

[PTC074]

Fc1 heavy chain
(SEQ ID NO: 4)

Fc1 light chain
(SEQ ID NO: 2)

Fc chain of Fc2
(SEQ ID NO: 7)

[PTC111]

(SEQ ID NO: 4)
Fc1 heavy chain (SEQ ID NO: 2)
Fc1 light chain

Fc chain of Fc2:
(SEQ ID NO: 9)
EPKSCDKTHTCPPCP APELLGGPSV FLFPPKPKDT LMISRTPEVT

CVVVDVSHED PEVKFNWYVD

GVEVHNAKTK PREEQYNSTY RVVSVLTVLH QDWLNGKEYK CKVSNKALPA

PIEKTISKAK

-continued

```
GQPREPQVYT FPPSRDELTK NQVSLSCAVK GFYPSDIAVE WESNGQPENN

YKTTPPVLDS

DGSFFLVSKL TVDKSRWQQG NVFSCSVMHE ALHNHYTQKS LSLSPGK
(Bold: L351F, bold and underlined: T366S, underlined: L368A, italic: Y407V)
```

Example 2. Comparison of Heterodimer-Forming Abilities of Fc Variants

Using the transient expression system constructed in Example 1 above, abilities to form Fc heterodimers, which are changed due to amino acid substitution of the CH3 domain, were compared, and thereby, high-efficiency Fc heterodimer variants were selected.

As an evaluation method, after performing non-reducing SDS-PAGE, the intensity of the PAGE bands corresponding to the heterodimers were measured and compared.

Specifically, the protein purified in Example 1 was reduced by 2-mercaptoethanol, or a sample without the 2-mercaptoethanol treatment was prepared. The reduced or non-reduced sample was electrophoresed by a SDS-PAGE method, and the intensity of the electrophoretic band was measured by using a ChemiDoc™ Imaging System (Bio-Rad) and Image Lab™ Software (Bio-Rad).

The Fc heterodimer formation ability according to the amino acid substitution of the CH3 domain was calculated with the measured band intensities, and the results are shown in Table 1 below.

TABLE 1

| Number | Mutation of amino acid Fc1 | Mutation of amino acid Fc2 | Expression level (mg/L) | Heterodimer ratio (%) |
|---|---|---|---|---|
| PTCWT (negative control group) | — | — | 269.5 ± 9.7 | 41.5 |
| PTC019 (positive control group) | T366W | T366S, L368A, Y407V | 183.3 ± 11.1 | 64.6 |
| PTC023 | L351F | L351G | 140.1 ± 4.8 | 27.2 |
| PTC024 | L351W | L351A | 112.3 ± 22.0 | 2.0 |
| PTC025 | L351W | L351G | 100.0 ± 18.5 | 15.4 |
| PTC031 | T394W | — | 253.8 ± 11.2 | 29.5 |
| PTC032 | T366W, T394H | T366S, L368A, Y407V | 143.8 ± 40.0 | 78.7 |
| PTC033 | T366W, T394F | T366S, L368A, Y407V | 162.7 ± 20.0 | 76.4 |
| PTC034 | T366W, T394W | T366S, L368A, Y407V | 211.8 ± 10.9 | 76.1 |
| PTC037 | L351F, T366W | L351A, T366S, L368A, Y407V | 193.4 ± 77.5 | 85.8 |
| PTC038 | L351W, T366W | L351A, T366S, L368A, Y407V | 142.8 ± 6.7 | 63.1 |
| PTC039 | L351F, T366W | L351G, T366S, L368A, Y407V | 151.2 ± 13.7 | 93.8 |
| PTC040 | L351W, T366W | L351G, T366S, L368A, Y407V | 146.1 ± 34.7 | 94.6 |
| PTC053 | L351F, T394H | L351A | 46.1 ± 4.8 | 1.0 |
| PTC054 | L351F, T394F | L351A | 50.6 ± 5.7 | 1.1 |
| PTC061 | L351F, T366W, T394H | L351A, T366S, L368A, Y407V | 73.2 ± 23.9 | 70.9 |
| PTC062 | L351F, T366W, T394F | L351A, T366S, L368A, Y407V | 32.7 ± 7.7 | 44.0 |
| PTC074 | T366W | L351G, T366S, L368A, Y407V | 125.9 ± 13.9 | 94.9 |
| PTC075 | T366W, T394H | L351G, T366S, L368A, Y407V | 33.4 ± 6.6 | 21.9 |
| PTC076 | L351F, T366W, T394H | L351G, T366S, L368A, Y407V | 34.9 ± 8.4 | 33.1 |
| PTC082 | L351V, T366W | L351A, T366S, L368A, Y407V | 55.0 ± 3.4 | 79.3 |
| PTC083 | L351I, T366W | L351A, T366S, L368A, Y407V | 42.6 ± 5.1 | <1 |
| PTC091 | T366W | L351A, T366S, L368A, Y407V | 52.1 ± 6.1 | 75.4 |
| PTC111 | T366W | L351F, T366S, L368A, Y407V | 55.8 ± 5.0 | 92.7 |
| PTC112 | T366W | L351W, T366S, L368A, Y407V | 30.9 ± 4.1 | <1 |
| PTC113 | L351A, T366W | L351F, T366S, L368A, Y407V | 146.3 ± 6.3 | 82.8 |
| PTC114 | L351A, T366W | L351W, T366S, L368A, Y407V | 22.0 ± 5.6 | <1 |
| PTC115 | L351G, T366W | L351F, T366S, L368A, Y407V | 79.4 ± 8.4 | <1 |
| PTC116 | L351G, T366W | L351W, T366S, L368A, Y407V | 23.1 ± 5.7 | <1 |

As a result, as shown in Table 1, the heterodimer formation rates of the negative control group (PTCWT) and the positive control group (PTC019) were 41.5% and 64.6%, respectively, whereas it was confirmed that heterodimer formation rates of PTC032, PTC033, PTC034, PTC037, PTC039, PTC040, PTC061, PTC074, PTC082, PTC091, PTC111 and PTC113 were respectively 78.7%, 76.4%, 76.1%, 85.8%, 93.8%, 94.6%, 70.9%, 94.9%, 79.3%, 75.4%, 92.7%, and 82.8%. In particular, it was confirmed that PTC039, PTC040, PTC074 and PTC111 had a ratio of Fc heterodimers exceeding 90%.

That is, an Fc variant according to an aspect may exhibit very excellent Fc heterodimer formation ability.

Example 3. Evaluation of Heterodimer-Forming Abilities of High Efficiency Fc Variants

3-1. SDS-PAGE Analysis

In order to evaluate heterodimer-forming abilities of the high-efficiency Fc variants selected in Example 2, SDS-PAGE analysis was performed in the same manner as in Example 2.

Specifically, intensities of the electrophoretic bands were measured from SDS-PAGE analysis. Thereafter, rates of Fc heterodimer formation according to the amino acid substitution of the CH3 domain were confirmed with the intensity of the measured bands, and the results are shown in Table 2 below (N/A: Not applicable).

In addition, as shown in Table 1, in cases of the negative control group (PTCWT) and the positive control group (PTC019), it was confirmed that not only the Fc1-2 hetero-dimer but also the Fc1-1 homo-dimer was formed at a rate of 17.1% with the negative control group (PTCWT), and Fc-2-2 homo-dimer was confirmed to be formed at a rate of 39.9% in the negative control group (PTCWT) and 13.3% in the positive control group (PTC019). On the other hand, in cases of the selected Fc variants of PTC039, PTC040, PTC074 and PTC111, it was confirmed that the formation rate of Fc1-1 homo-dimers and Fc-2-2 homo-dimers was low, and the formation rate of Fc1-2 hetero-dimers was noticeably higher.

That is, it may be seen that the Fc variant according to an aspect is capable of selectively forming Fc1-2 hetero-dimers.

3-2. CE-SDS Analysis

In order to verify heterodimer-forming abilities of the high-efficiency Fc variants selected in Example 2, capillary electrophoresis-SDS (CE-SDS) analysis was performed.

Specifically, capillary electrophoresis was performed by using a PA 800 Plus™ pharmaceutical analysis system (SCIEX) to verify Fc heterodimer formation rates of the Fc variants, and the results are shown in Table 3 below.

TABLE 2

| Note | Molecular Weight (kDa) | PTCWT | PTC019 | PTC039 | PTC040 | PTC074 | PTC111 |
|---|---|---|---|---|---|---|---|
| Multimer | N/A | <1 | <1 | <1 | <1 | <1 | <1 |
| Fc1-1 homo-dimer | 146.8 | 17.1 | <1 | 2.1 | 1.1 | 0.7 | <1 |
| Fc1-2 hetero-dimer | 99.3 | 41.5 | 64.6 | 93.8 | 94.6 | 94.9 | 92.7 |
| Fc1 monomer | 73.4 | 1.5 | 2.4 | 3.3 | 3.4 | 3.6 | 5.2 |
| Fc-2-2 homo-dimer | 51.8 | 39.9 | 13.3 | <1 | <1 | <1 | <1 |
| Fc2 monomer | 25.9 | <1 | 19.7 | <1 | <1 | <1 | <1 |
| Free light chain | 23.7 | <1 | <1 | <1 | <1 | <1 | |

FIG. 1 is an image showing results of SDS-PAGE analysis of Fc variants.

As a result, as shown in FIG. 1, it was confirmed that the band intensity of the Fc1-1 homo-dimer (146.8 kDa) of the selected PTC039, PTC040, PTC074 and PTC111 was noticeably reduced compared to that of the negative control group (PTCWT), and the band intensity of the Fc2 monomer (25.9 kDa) was noticeably reduced compared to the positive control group (PTC019). On the other hand, it was confirmed that the Fc1-2 hetero-dimer was formed with high efficiency at 99.3 kDa.

TABLE 3

| Note | Molecular Weight (kDa) | PTCWT | PTC019 | PTC039 | PTC040 | PTC074 | PTC111 |
|---|---|---|---|---|---|---|---|
| Fc1-1 homo-dimer | 144.0 | 11.1 | n.d. | n.d. | n.d. | n.d. | n.d. |
| Fc1-2 hetero-dimer | 98.0 | 40.1 | 60.1 | 81.0 | 80.2 | 83.8 | 84.8 |
| Light chain free Fc1-2 hetero-dimer | 75.2 | 4.8 | 2.5 | 3.8 | 7.7 | 8.5 | 6.6 |
| Fc1 monomer | 71.9 | 0.5 | 0.3 | 1.0 | 1.4 | 0.6 | 0.4 |
| Fc-2-2 homo-dimer | 49.2 | 34.4 | 13.7 | n.d. | n.d. | n.d. | 0.6 |
| Fc2 monomer | 24.6 | n.d. | 20.3 | 11.3 | 7.5 | 2.4 | 2.0 |
| Free light chain | 22.8 | 2.5 | 0.4 | 1.8 | 2.3 | 2.7 | 2.0 |

Figure 2:
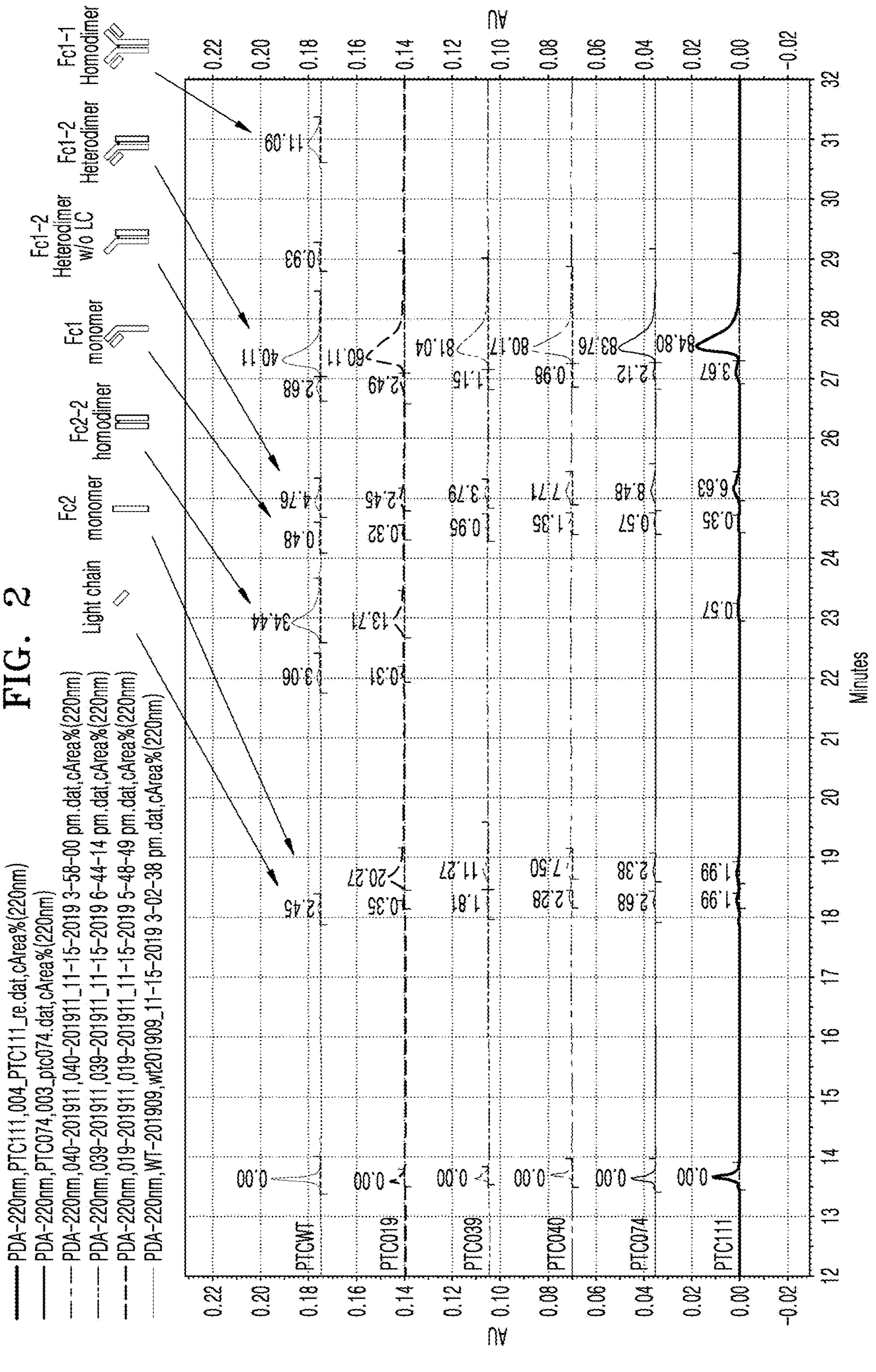
FIG. 2 is a graph showing results of capillary electrophoresis-SDS (CE-SDS) analysis of Fc variants.

FIG. 2 is a graph showing results of capillary electrophoresis-SDS (CE-SDS) analysis of Fc variants.

As a result, as shown in FIG. 2, at around 23 minutes of retention time, Fc-2-2 homo-dimer formation rate of the negative control group (PTCWT) was shown to be 34.44%, and Fc-2-2 homo-dimer formation rate of the positive control group (PTC019) was confirmed to be 13.71%. On the other hand, in cases of PCT039, PTC040, and PTC074, Fc-2-2 homo-dimer was not formed, and in case of PCT111, Fc-2-2 homo-dimer formation rate was 0.57%, and the rate was noticeably lower compared to that of the negative control group (PTCWT) and the positive control group (PCT019).

In addition, as shown in Table 2, heterodimer formation rates of PTC039, PTC040, PTC074 and PTC111 were 81.0%, 80.2%, 83.8% and 84.8%, respectively, and were significantly higher than that of the negative control group (PCTWT) and the positive control group (PTC019).

That is, it may be seen that the Fc variant according to an aspect has excellent heterodimer formation ability.

3-3. SE-HPLC Analysis

In order to verify the heterodimer-forming abilities of the high-efficiency Fc variants selected in Example 2, size exclusion-high-performance liquid chromatography (SE-HPLC) analysis was performed, and the results are shown in Table 4 below.

TABLE 4

| Note | Retention time (min) | PTCWT | PTC019 | PTC039 | PTC040 | PTC074 | PTC111 |
|---|---|---|---|---|---|---|---|
| Multimer | 11.4 | 0.4 | 16.5 | 4.7 | 5.9 | 2.9 | 4.0 |
| Fc1-1 homo-dimer | 16.0 | 10.86 | | | | | 0.6 |
| Fc1-2 hetero-dimer | 17.0 | 42.16 | 58.24 | 90.76 | 87.51 | 90.59 | 91.6 |
| Fc1 monomer | N/A | | | | | | |
| Fc-2-2 homo-dimer | 18.4 | 46.03 | 13.13 | | 1.5 | 0.96 | 2.7 |
| Fc2 monomer | 19.2 | | 25.78 | | | | 1.0 |
| Free light chain | 19.8 | | | | | | |

FIGS. 3A to 3F are graphs showing results of size exclusion-high-performance liquid chromatography (SE-HPLC) analysis of PTCWT, PTC019, PTC039, PTC040, PTC074, and PTC111, respectively.

Figure 3A:
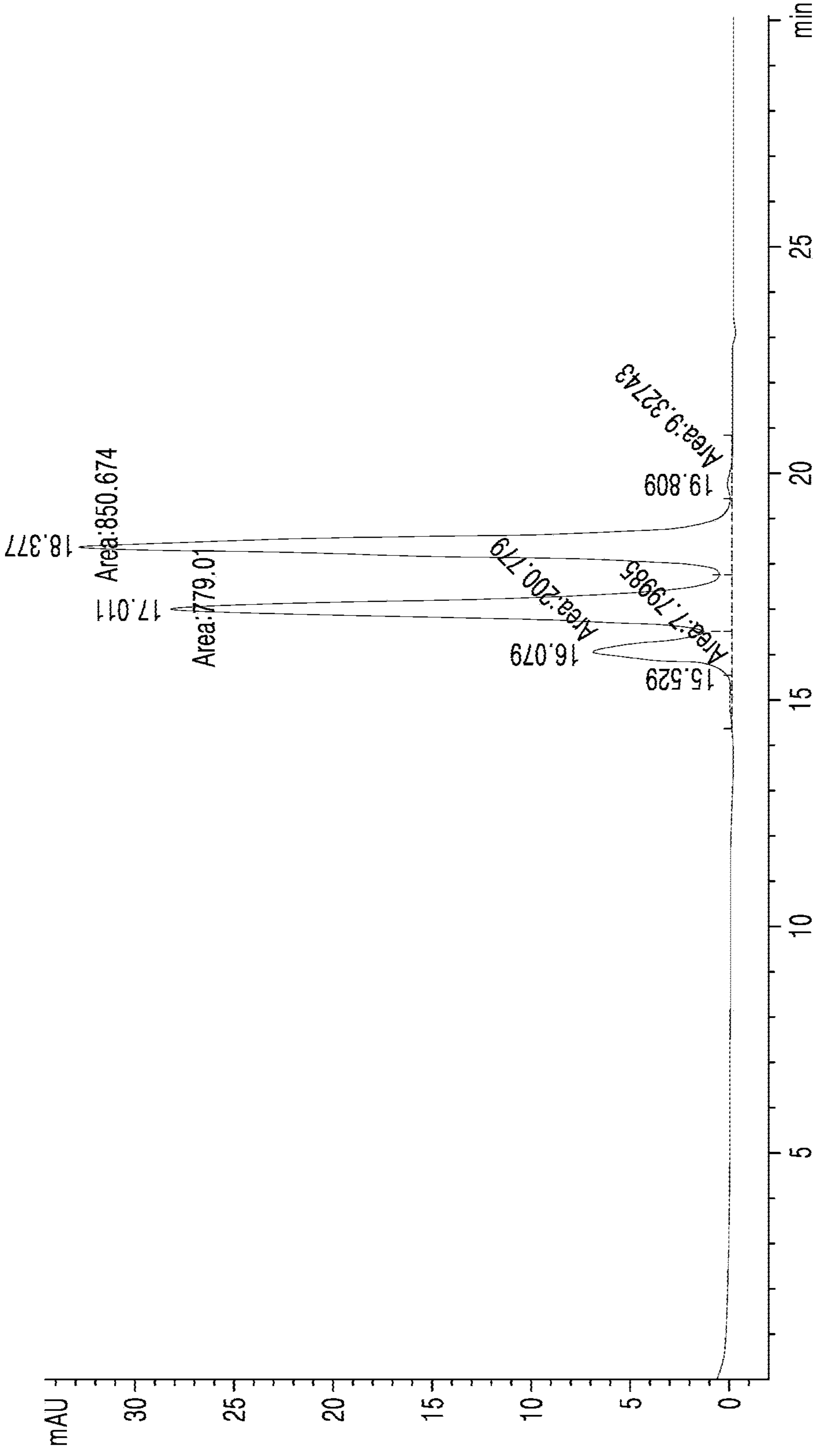
FIGS. 3A to 3F are graphs showing results of size exclusion-high-performance liquid chromatography (SE-HPLC) analysis of PTCWT, PTC019, PTC039, PTC040, PTC074, and PTC111, respectively.
Figure 3B:
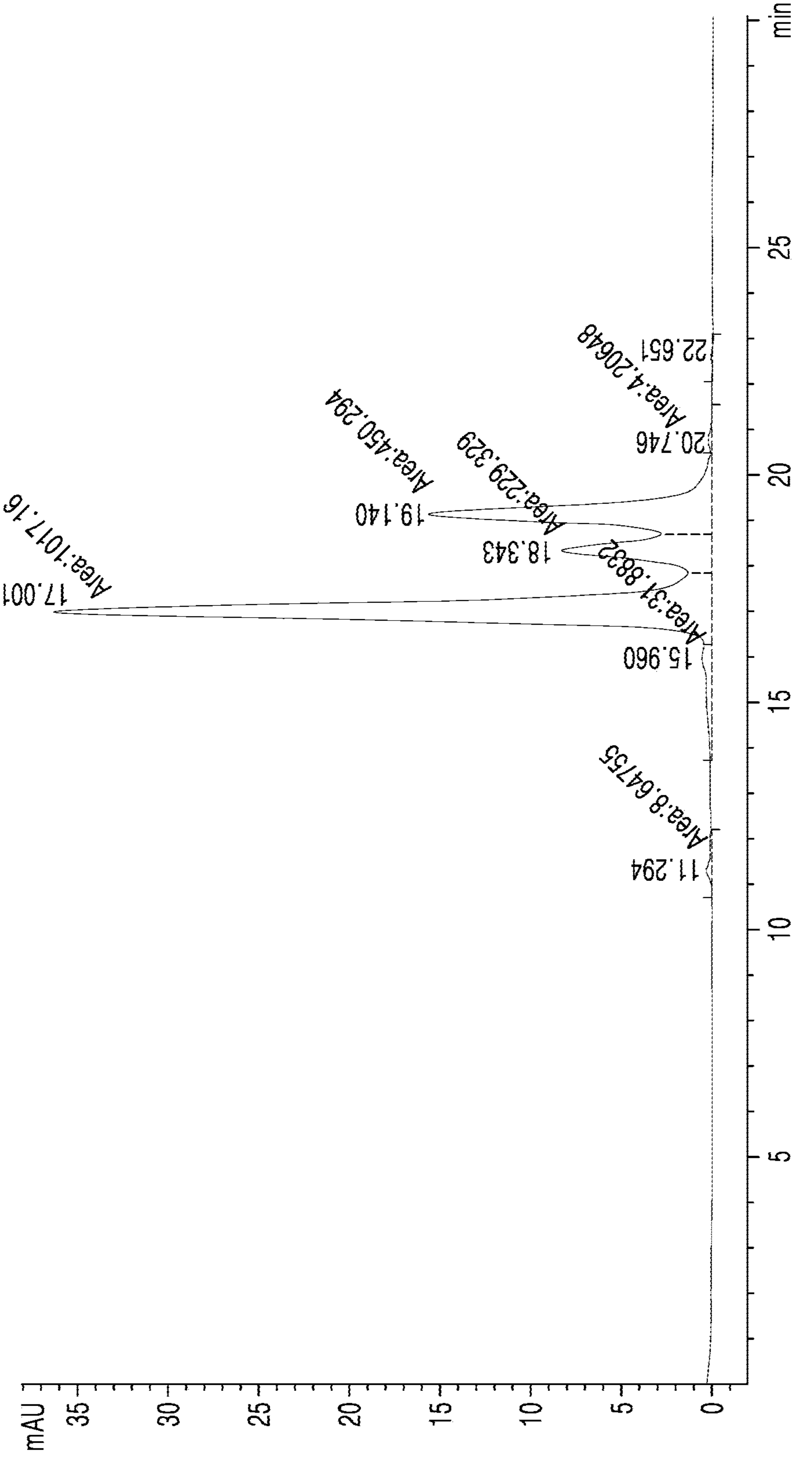
Figure 3C:
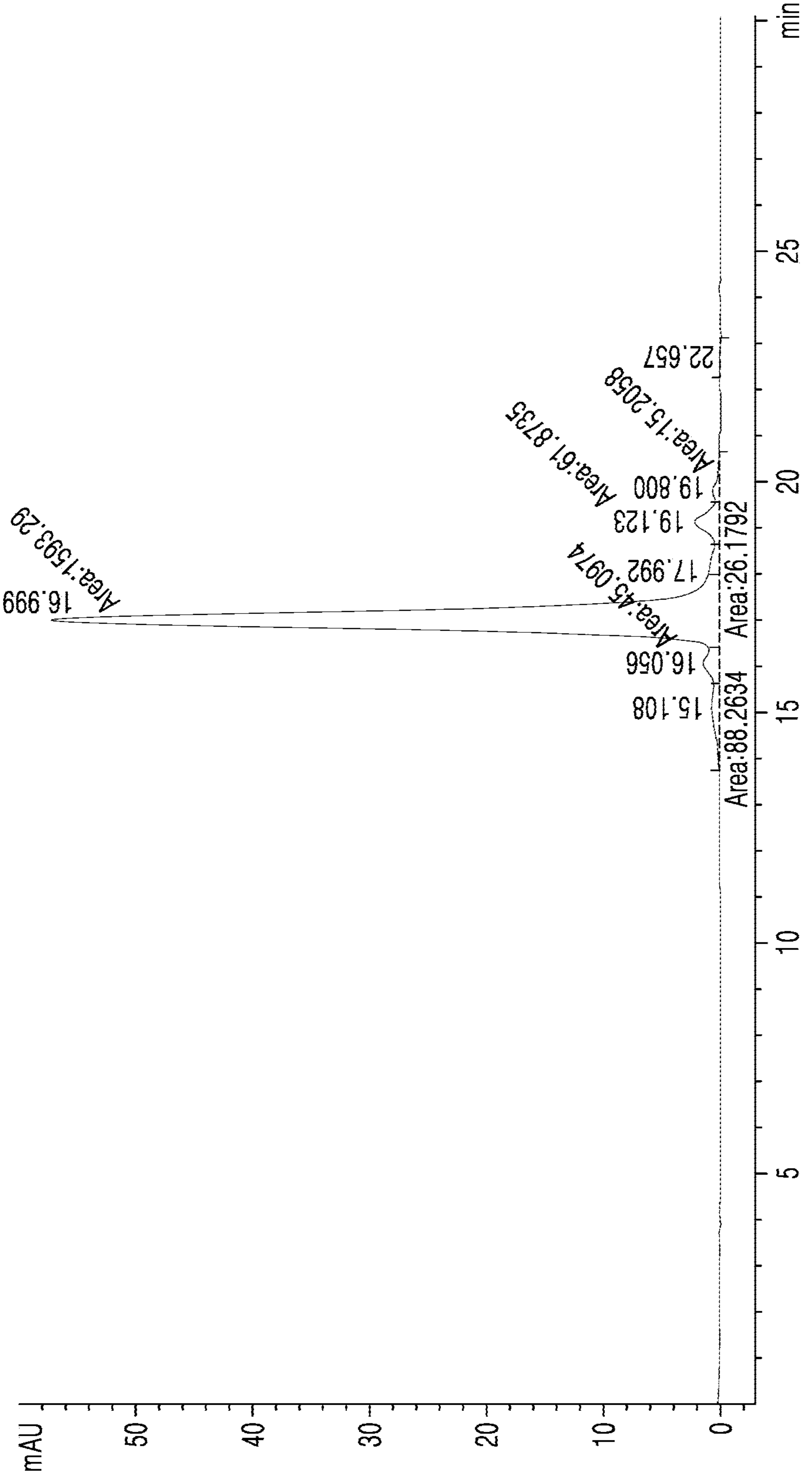
Figure 3D:
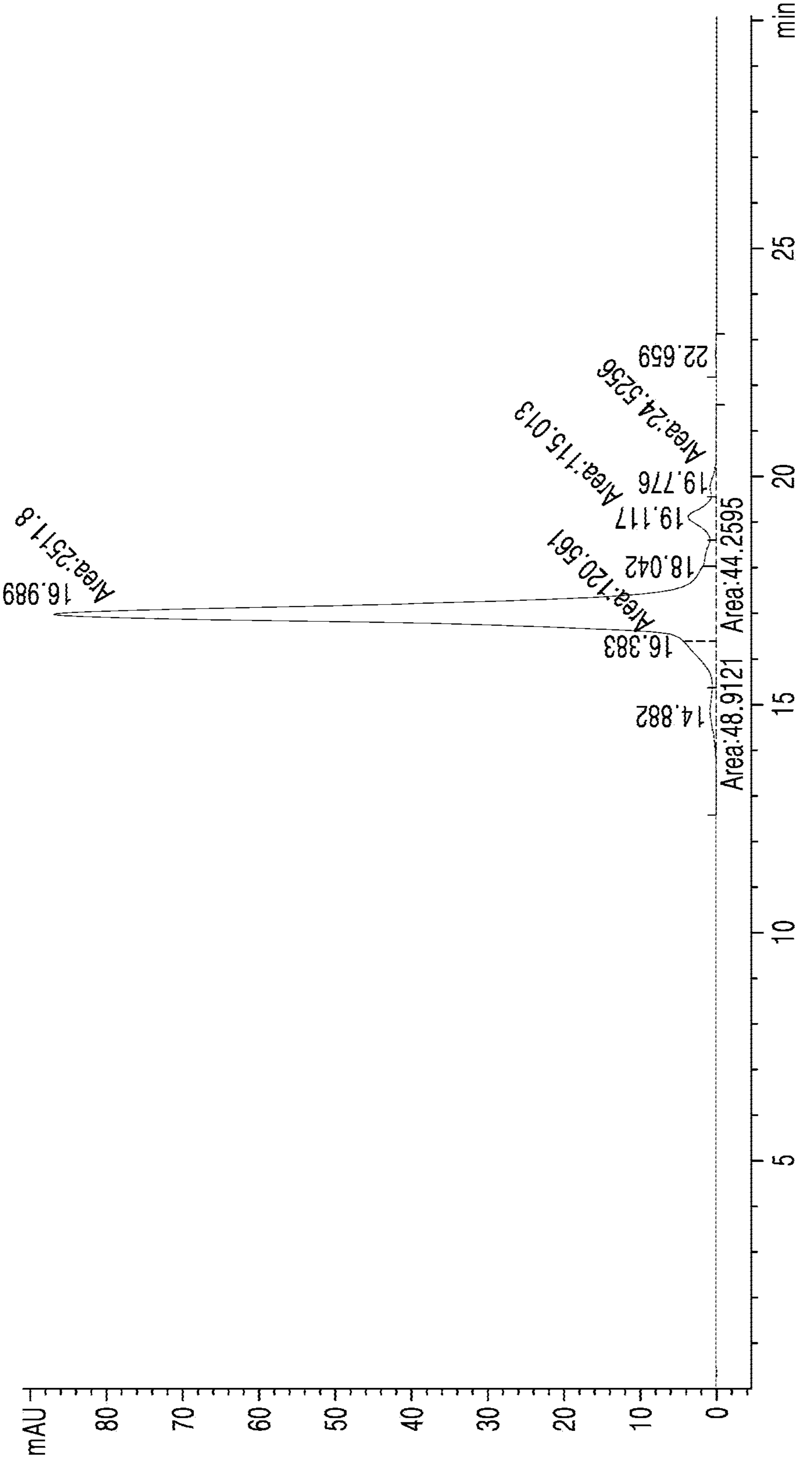
Figure 3E:
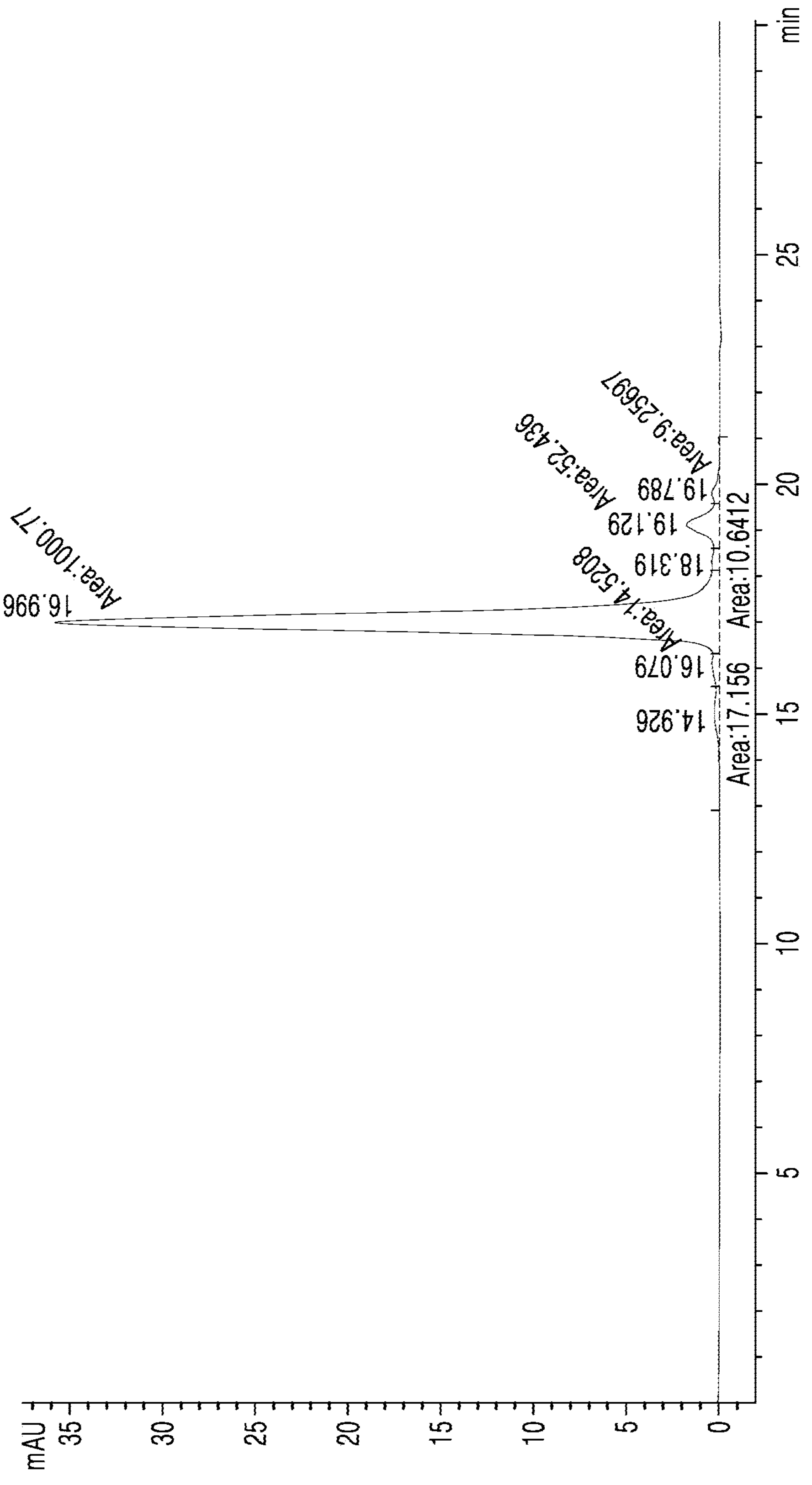
Figure 3F:
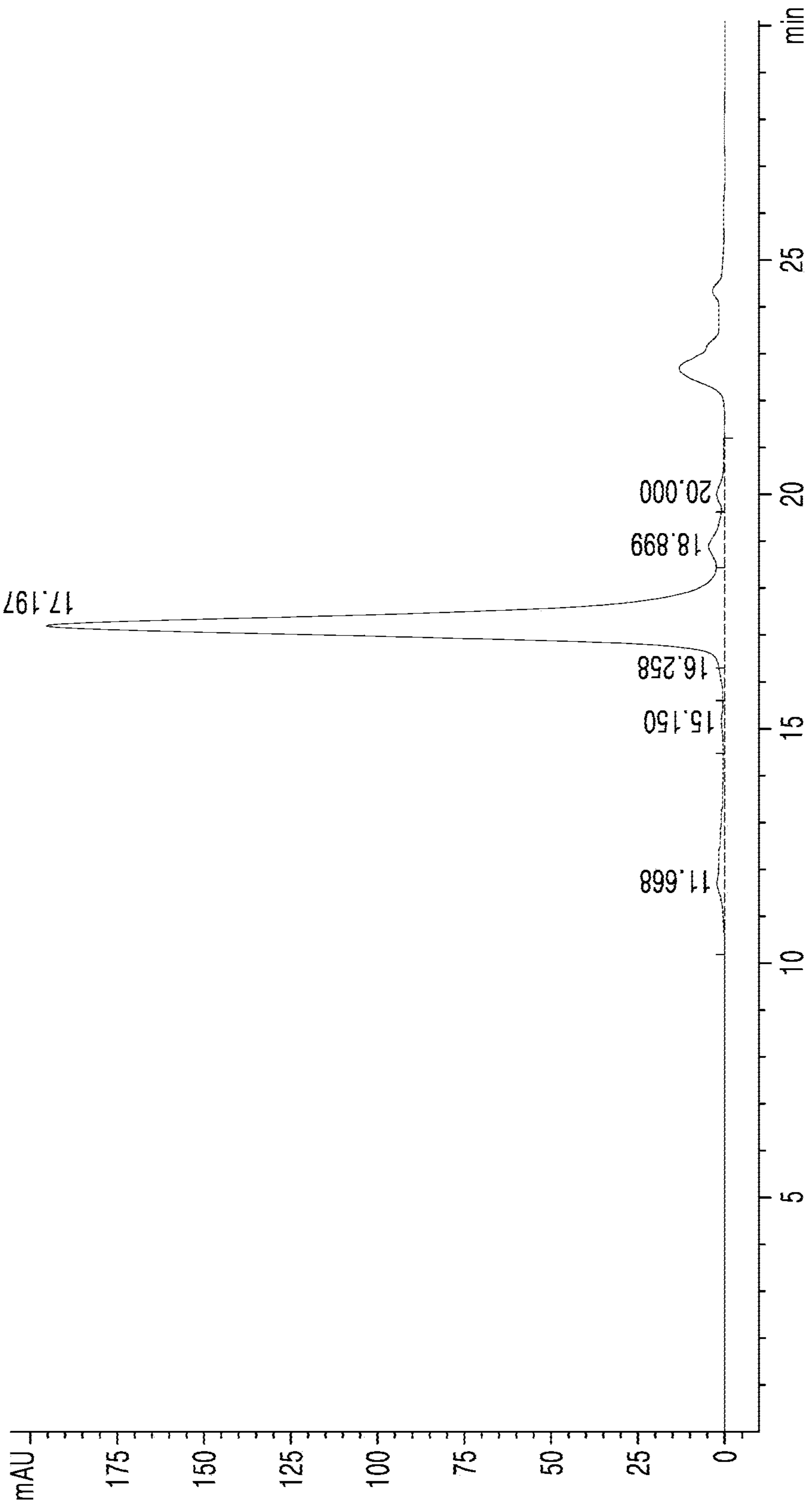

As a result, as shown in FIGS. 3A to 3F, in SE-HPLC analysis of the protein purified with Protein A, main peaks of a heterodimer were observed at retention times of 16.989 minutes to 17.197 minutes in Fc variants including the negative control group (PTCWT) and the positive control group (PTC019). Specifically, in case of the negative control group (PTCWT), an Fc-1-1 homo-dimer peak was observed at a retention time of 16.079 minutes and an Fc2-2 homo-dimer peak was observed at 18.377 minutes (FIG. 3A). In addition, in case of the positive control group (PTC019), an Fc-2-2 homo-dimer peak was observed at a retention time of 18.343 minutes and an Fc-2 monomer peak was observed at 19.14 minutes (FIG. 3B). That is, in case of the negative control group (PTCWT) and the positive control group (PCT019), heterodimer formation rate was confirmed to be low as multiple peaks including the Fc1-2 hetero-dimer were shown, on the other hand, in case of the Fc variants of PTC039, PTC040, PTC074 and PTC111, the main peak was observed in a form of a single peak. That is, in case of the selected Fc variants, heterodimer formation rate was confirmed to be excellent compared to that of the negative control group (PTCWT) and the positive control group (PTC019).

In addition, as shown in Table 4, it was confirmed that the selected Fc variants of PTC039, PTC040, PTC074 and PTC111 had better heterodimer formation abilities compared to the two control groups of PTCWT and PTC019.

Therefore, the Fc variant according to an aspect may form a heterodimer with high efficiency, and thus bispecific antibodies may be easily prepared.

Example 4. Evaluation of Thermodynamic Stability of High-Efficiency Fc Variant Heterodimers In order to indirectly confirm structural stabilities of the heterodimers of the high-efficiency Fc variants identified in Example 3, a thermodynamic stability evaluation was performed by using differential scanning calorimetry (DSC).

Specifically, thermal stabilities of the selected Fc variants were measured by using Nano DSC™ (TA instruments), and melting temperatures (Tm, ° C.) were calculated. The calculated melting points of the Fc variants are shown in Table 5 below.

TABLE 5

| | Tm (° C.) | | |
|---|---|---|---|
| Fc variant | CH3 | CH2 | Fab |
| PTCWT | 82.75 | 69.01 | 71.88 |
| PTC019 | 70.82 | 57.14 | 71.82 |
| PTC039 | 77.51 | 65.92 | 69.63 |
| PTC040 | 77.75 | 66.63 | 69.82 |
| PTC074 | 77.72 | 66.84 | 69.68 |
| PTC111 | 76.87 | 70.36 | 71.54 |

As a result, as shown in Table 5, it was confirmed that the selected Fc variants of PTC039, PTC040, PTC074 and PTC111 had somewhat unstable thermal stability compared to the wild-type Fc heterodimer (PTCWT), but had relatively high thermodynamic stability compared to the KiH Fc heterodimer (PTC019) of Genentech.

That is, the Fc variant according to an aspect has excellent heterodimer-forming ability as well as excellent thermodynamic stability, thus, formation of stable bispecific antibodies is possible.

Example 5. Comparison of Heterodimer-Forming Abilities of Variants Substituted with Reverse-Sequence in CH3 Domain of High-Efficiency Fc Variants In order to evaluate heterodimer-forming abilities of variants substituted with reverse-sequence in CH3 domain of high-efficiency Fc variants selected in Example 3 above, SDS-PAGE analysis was performed in the same manner as in Example 2.

Fc heterodimer formation abilities according to the amino acid substitution in the CH3 domain were calculated with the band intensities measured from SDS-PAGE analysis, and the results are shown in Table 6 below.

TABLE 6

| Number | Mutation of amino acid Fc1 | Mutation of amino acid Fc2 | Expression level (mg/L) | Heterodimer ratio (%) |
|---|---|---|---|---|
| PTCWT (negative control group) | — | — | 147.2 ± 37.7 | 40.9 |
| PTC019 (positive control group) | T366W | T366S, L368A, Y407V | 118.3 ± 39.6 | 64.7 |
| PTC088 | L351G, T366S, L368A, Y407V | L351F, T366W | 102.1 ± 20.2 | 72.1 |
| PTC089 | L351G, T366S, L368A, Y407V | L351W, T366W | 92.2 ± 8.9 | 83.3 |
| PTC090 | L351G, T366S, L368A, Y407V | T366W | 41.5 ± 3.6 | 92.1 |

Figure 4:
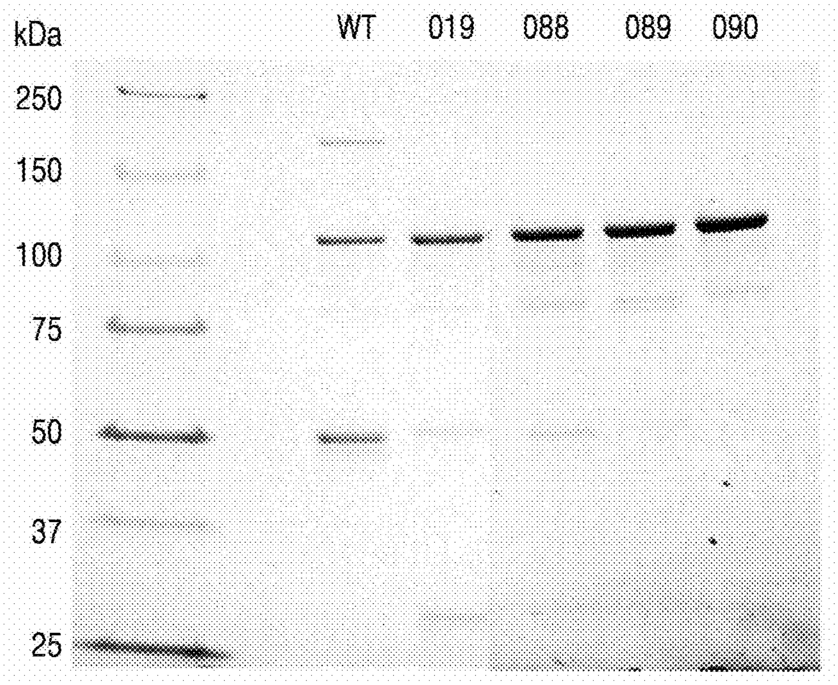
FIG. 4 is an image showing results of SDS-PAGE analysis of reverse sequence substitution Fc variants (M: size marker, WT: PTCWT (negative control group), 019: PTC019 (positive control group), 088: PTC088, 089: PTC089, 090: PTC090).

FIG. 4 is an image showing results of SDS-PAGE analysis of reverse sequence substitution Fc variants (M: size marker, WT: PTCWT (negative control group), 019: PTC019 (positive control group), 088: PTC088, 089: PTC089, 090: PTC090).

As a result, as shown in FIG. 4, it was confirmed that the reverse sequence substitution Fc variants did not form a band around 150 kDa compared to the negative control group (PTCWT), and a bands was weakly formed at 49.2 kDa. That is, it was confirmed that the reverse sequence substitution Fc variants did not form a Fc-1-1 homo-dimer, and formation of Fc-2-2 homo-dimers was reduced. In addition, it was confirmed that a band was weakly formed in the vicinity of 25 kDa compared to the positive control group (PCT019). That is, it may be seen that the reverse sequence substitution Fc variants have reduced Fc-2 monomer formation, and show heterodimer formation rates similar to that of PTC039, PTC040, and PTC074 (see FIG. 1).

In addition, as shown in Table 6, the heterodimer formation rates of the negative control group (PTCWT) and the positive control group (PTC019) were shown to be 40.9% and 64.7%, respectively, whereas it was confirmed that PTC088, PTC089 and PTC090, which are reverse sequence substitution Fc variants of PTC039, PTC040 and PTC074, exhibited heterodimer formation rates of 72.1%, 83.3% and 92.1%, respectively.

Therefore, it may be seen that the reverse sequence substitution variants of the Fc variant according to an aspect forms a heterodimer in a similar ratio before and after substitution. In addition, since the reverse sequence substitution variants of the Fc variants have an excellent heterodimer formation rate, Fc variants may be formed with high efficiency regardless of whether the sequence inserted into Fc1 or Fc2 is substituted or not.

Example 6. Comparison of Heterodimer-Forming Abilities of Fc Variants with Sequence Change at Position 351 of CH3 Domain In order to evaluate heterodimer-forming ability of variants, in which the position 351 of the CH3 domain is substituted with an amino acid having similar properties, like PTC074 and PTC111, which are high-efficiency Fc variants selected in Example 3, SDS-PAGE analysis was performed in the same manner as in Example 2.

Fc heterodimer-forming abilities according to the amino acid substitution in the CH3 domain were calculated with the intensity of the bands measured from SDS-PAGE analysis, and the results are shown in Table 7 below.

TABLE 7

| Number | Mutation of amino acid Fc1 | Mutation of amino acid Fc2 | Expression level (mg/L) | Heterodimer ratio (%) |
|---|---|---|---|---|
| PTCWT (negative control group) | — | — | 54.4 ± 5.6 | 40.2 |
| PTC019 (positive control group) | T366W | T366S,L368A, Y407V | 51.1 ± 5.6 | 79.7 |
| PTC074 | T366W | L351G,T366S, L368A, Y407V | 40.4 ± 4.1 | 93.5 |
| PTC097 | T366W | L351V,T366S, L368A, Y407V | 39.8 ± 9.9 | 82.7 |
| PTC098 | T366W | L351S,T366S, L368A, Y407V | 26.4 ± 12.7 | 76.8 |
| PTC099 | T366W | L351M,T366S, L368A, Y407V | 20.9 ± 1.9 | 86.5 |
| PTC111 | T366W | L351F,T366S, L368A, Y407V | 55.8 ± 5.0 | 92.7 |
| PTC112 | T366W | L351W,T366S, L368A, Y407V | 30.9 ± 4.1 | <1 |

Figure 5:
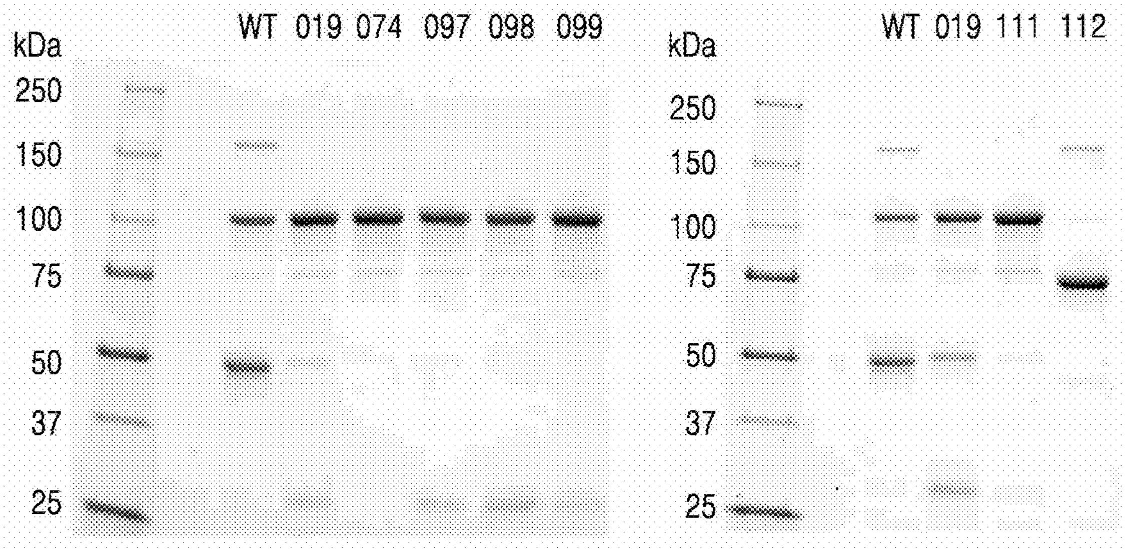
FIG. 5 is an image showing results of SDS-PAGE analysis of Fc variants in which a portion of the sequence is substituted (M: size marker, WT: PTCWT (negative control group), 019: PTC019 (positive control group), 074: PTC074, 097: PTC097, 098: PTC098, 099: PTC099, 111: PTC111, 113: PTC113).

FIG. 5 is an image showing results of SDS-PAGE analysis of Fc variants, in which a portion of the sequence is substituted (M: size marker, WT: PTCWT (negative control group), 019: PTC019 (positive control group), 074: PTC074, 097: PTC097, 098: PTC098, 099: PTC099, 111: PTC111, 113: PTC113).

As a result, as shown in FIG. 5, in cases of PTC074 and PTC111, it was confirmed that a band was not formed around 150 kDa compared to the negative control group (PTCWT), and compared to the positive control group (PTC019), intensity of the bands at 49.2 kDa and 24.6 kDa were noticeably reduced. In addition, it was confirmed that the intensity of the bands at 24.6 kDa was noticeably reduced compared to PTC097, PTC098, and PTC099, in which the sequence is substituted at position 351 of Fc-2. On the other hand, it was confirmed that the intensity of the band increased at 98 kDa, which is the expected molecular weight of the Fc-1-2 heterodimer.

In addition, as shown in Table 7, the heterodimer formation rates of PTC074, PTC097, PTC099 and PTC111 were shown to be 93.5%, 82.7%, 86.5%, and 92.7%, respectively, and were confirmed to be significantly higher than that of the negative control group (PCTWT) and the positive control group (PTC019). In particular, in cases of PTC074 and PTC111, in which the position 351 of the CH3 domain was substituted with glycine (G) or phenylalanine (F), it was confirmed that the Fc heterodimer formation rate exceeded 90%.

That is, it may be seen that the Fc variant according to an aspect has excellent Fc heterodimer-forming ability by substituting the position 351 of the CH3 domain with a specific amino acid.

Example 7. Evaluation of Heterodimer-Forming Ability of Bispecific Antibodies Including High-Efficiency Fc Variants 7-1. Fab-Fc×scFv-Fc Bispecific Antibody In order to evaluate heterodimer formation rate of the hetero-bispecific antibody including the high-efficiency Fc variants selected in Example 3, the first polypeptide was designed to express an IgG chain (Fc1) of an intact form, in which both the heavy chain and the light chain are linked, and the second polypeptide was designed to express a scFV-Fc form (Fc2). Thereafter, expression of Fc1 was proceeded based on an Avelumab antibody (Bavencio, Pfizer) including an IgG1 Fc region, and Fc2 was expressed in a scFv form including an IgG1 Fc region based on an anti-CD3 scFv sequence of blinatumomab.

For comparison, a Fab-Fc×scFv-Fc hetero-bispecific antibody, in which anti-CD3 scFv of blinatumomab is bound to Fc2 of an Fc variant having a wild-type CH3 domain sequence (corresponding to "PTCWT" in Table 1), was used as a negative control group, and a Fab-Fc×scFv-Fc hetero-bispecific antibody, in which anti-CD3 scFv of blinatumomab is bound to Fc2 of an Fc variant (corresponding to "PTC019" in Table 1) having Genentech's knobs-into-hole (KiH) sequence in the CH3 domain, was used as a positive control group.

Expression of each test substance was carried out by using the transient expression system constructed in Example 1, and after performing non-reducing SDS-PAGE, the intensities of the PAGE bands corresponding to the heterodimers were measured to compare the rates of heterodimer formation.

Fc heterodimer formation ability according to the amino acid substitution of the CH3 domain was calculated with the measured band intensity, and the results are shown in Table 8 below.

TABLE 8

| Note | Molecular Weight (kDa) | CH3 domain sequence of Fab-Fc × scFv-Fc hetero-bispecific antibody | | |
|---|---|---|---|---|
| | | PTCWT | PTC019 | PTC074 |
| Fc1-1 homo-dimer | 144.0 | 17.6 | <1 | <1 |
| Fd-2 hetero-dimer | 124.4 | 45.4 | 75.8 | 88.8 |
| Fc-2-2 homo-dimer | 104.8 | 37.0 | 19.6 | 7.0 |
| Light chain free Fc1-2 hetero-dimer | 101.6 | <1 | <1 | <1 |
| Fc 2 or Fc 1 heavy chain | ~50 | <1 | 4.6 | 4.2 |

Figure 6:
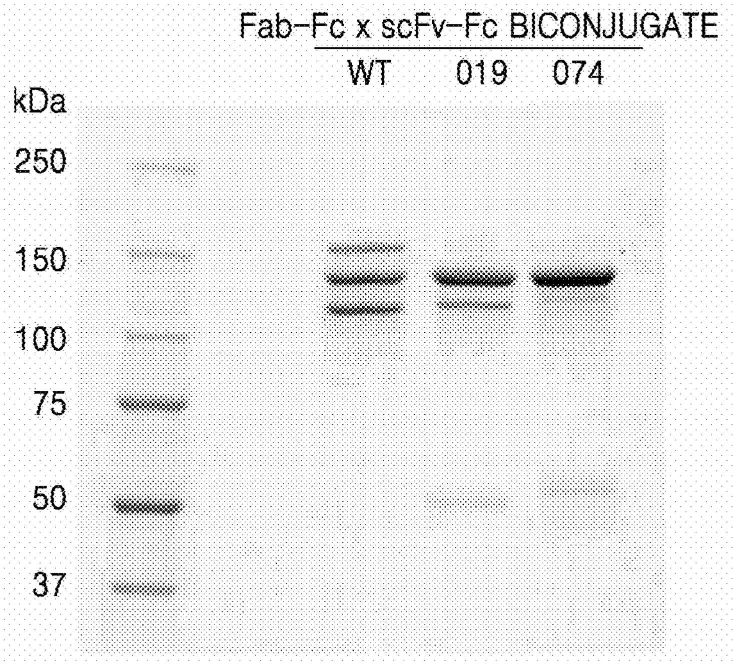
FIG. 6 is an image showing results of SDS-PAGE analysis of Fab-Fc×scFv-Fc biconjugates (M: size marker, WT: Fab-Fc×scFv-Fc biconjugate with a PTCWT sequence applied to a CH3 domain (negative control group), 019: Fab-Fc×scFv-Fc biconjugate with a PTC019 sequence applied to a CH3 domain (positive control group), 074: Fab-Fc×scFv-Fc biconjugate with a PTC074 sequence applied to a CH3 domain).

FIG. 6 is an image showing results of SDS-PAGE analysis of Fab-Fc×scFv-Fc biconjugates (M: size marker, WT: Fab-Fc×scFv-Fc biconjugate with a PTCWT sequence applied to the CH3 domain (negative control group), 019: Fab-Fc×scFv-Fc biconjugate with a PTC019 sequence applied to the CH3 domain (positive control group), 074: Fab-Fc×scFv-Fc biconjugate with a PTC074 sequence applied to the CH3 domain).

As a result, as shown in FIG. 6, it was confirmed that the Fab-Fc×scFv-Fc hetero-bispecific antibody to which a PTC074 sequence was applied did not form a band at 144 kDa compared to the hetero-bispecific antibody to which a sequence of the negative control group (PTCWT) was applied. In addition, it was confirmed that the intensity of the band was reduced at 104.8 kDa compared to the hetero-bispecific antibody to which a PTC019 sequence was applied. On the other hand, at 124.4 kDa, which is the expected molecular weight of the complete Fab-Fc×scFv-Fc hetero-bispecific antibody, it was confirmed that the band intensity was increased compared to the negative control group (PCTWT) and the positive control group (PTC019).

In addition, as shown in Table 8, the Fc1-2 heterodimer formation rate of the Fab-Fc×scFv-Fc hetero-bispecific antibody, which has a CH3 domain sequence of PTC074, was 88.8%, and it was confirmed that the heterodimer formation rate was significantly higher than that of the negative control group (PTCWT) and the positive control group (PTC019).

That is, it may be seen that the Fc variant according to an aspect may be applied as a hetero-bispecific antibody structure that forms antibodies of different structures and has excellent heterodimer formation ability.

7-2. Fab-Fc×scFv-scFv-Fc Bispecific Antibody

The rates of heterodimer formation were evaluated in the same manner as in Example 7-1, except that Fab-Fc×scFv-scFv-Fc bispecific antibodies designed to express the second polypeptide in a form of scFv-scFv-Fc (Fc2) were used, and Fc2 was expressed in a form of double scFv (scFv×scFv) including an IgG1 Fc region, based on the anti-CD3 scFv sequence of blinatumomab and the VH-VL sequence of Bevacizumab (Avastin, Roche).

For comparison, a Fab-Fc×scFv-scFv-Fc hetero-bispecific antibody, in which double scFv is bound to Fc2 of an Fc variant having a wild-type CH3 domain sequence (corresponding to "PTCWT" in Table 1), was used as a negative control group, and a Fab-Fc×scFv-scFv-Fc hetero-bispecific antibody, in which double scFv is bound to Fc2 of an Fc variant (corresponding to "PTC019" in Table 1) having Genentech's knobs-into-hole (KiH) sequence in the CH3 domain, was used as a positive control group.

TABLE 9

| Note | Molecular Weight (kDa) | CH3 domain sequence of Fab-Fc × scFv-scFv-Fc hetero-bispecific antibody | | |
|---|---|---|---|---|
| | | PTCWT | PTC019 | PTC074 |
| Fc2-2 homo-dimer | 196.0 | 9.7 | 5.6 | <1 |
| Fc1-2 hetero-dimer | 167.8 | 42.0 | 57.6 | 70.2 |
| Fc-1-1 homo-dimer | 161.7 | 37.0 | <1 | <1 |
| Unknown 1 | 159.1 | <1 | 3.5 | 2.6 |
| Unknown 2 | ~140~150 | 11.3 | 15.7 | 19.0 |
| Unknown 3 | 112.9 | <1 | 2.8 | 3.4 |
| Fc 1 or 2 monomer | ~70~80 | <1 | 14.7 | 4.7 |

Figure 7:
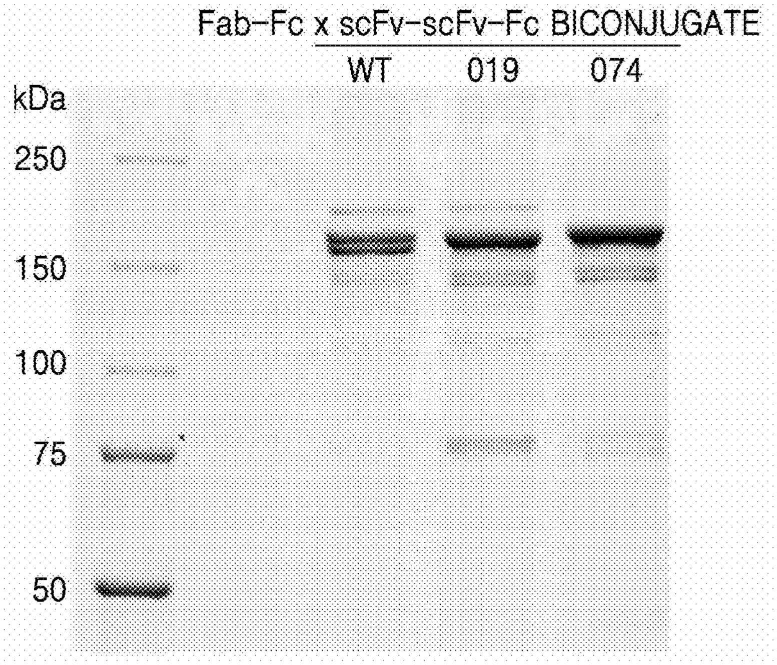
FIG. 7 is an image showing results of SDS-PAGE analysis of Fab-Fc×scFv-scFv-Fc biconjugates (M: size marker, WT: Fab-Fc×scFv-scFv-Fc biconjugate with a PTCWT sequence applied to a CH3 domain (negative control group), 019: Fab-Fc×scFv-scFv-Fc biconjugate with a PTC019 sequence applied to a CH3 domain (positive control group), 074: Fab-Fc×scFv-scFv-Fc biconjugate with a PTC074 sequence applied to a CH3 domain).

FIG. 7 is an image showing results of SDS-PAGE analysis of Fab-Fc×scFv-scFv-Fc biconjugates (M: size marker, WT: Fab-Fc×scFv-scFv-Fc biconjugate with a PTCWT sequence applied to the CH3 domain (negative control group), 019: Fab-Fc×scFv-scFv-Fc biconjugate with a PTC019 sequence applied to the CH3 domain (positive control group), 074: Fab-Fc×scFv-scFv-Fc biconjugate with a PTC074 sequence applied to the CH3 domain).

As a result, as shown in FIG. 7, the Fab-Fc×scFv×scFv-Fc biconjugate to which a PTC074 sequence was applied was confirmed to have a noticeably decreased intensity of the 196 kDa band compared to the conjugate to which the negative control group (PTCWT) and the positive control group (PTC019) sequences were applied. In addition, since the band intensities were reduced, except in the band of the heterodimer shown in the biconjugate to which a positive control group (PTC019) sequence was applied, it was confirmed that the target Fc 1-2 hetero-dimer of 167.8 kDa was formed with high efficiency.

In addition, as shown in Table 9, the Fc1-2 heterodimer formation rate of the Fab-Fc×scFv-scFv-Fc hetero-bispecific antibody having a CH3 domain sequence of PTC074 was 70.2%, and it was confirmed that the heterodimer formation rate was significantly higher than that of the negative control group (PTCWT) and the positive control group (PTC019).

That is, it may be seen that the Fc variant according to an aspect is not only easy to apply as a hetero-bispecific antibody structure having a large molecular weight structure because several structures are connected, but also has excellent heterodimer formation when applied as the structure.

7-3. Fab-Fc×Cytokine-Fc Bispecific Antibody

The rates of heterodimer formation were evaluated in the same manner as in Example 7-1, except that Fab-Fc× cytokine-Fc bispecific antibodies designed to express the second polypeptide in a form of cytokine-Fc (Fc2) were used, and expression of Fc2 was proceeded in a form of a cytokine including an IgG1 Fc region, which is based on interleukine-2 (IL-2, aldesleukine) sequence.

For comparison, a Fab-Fc×IL-2v-Fc hetero-bispecific antibody, in which an IL-2 variant (IL-2v) is bound to Fc2 of an Fc variant having a wild-type CH3 domain sequence (corresponding to "PTCWT" in Table 1), was used as a negative control group, and a Fab-Fc×IL-2v-Fc hetero-bispecific antibody, in which an IL-2 variant (IL-2v) is bound to Fc2 of an Fc variant (corresponding to "PTC019" in Table 1) having Genentech's knobs-into-hole (KiH) sequence in the CH3 domain, was used as a positive control group.

TABLE 10

| Note | Molecular Weight (kDa) | CH3 domain sequence of Fab-Fc × cytokine-Fc hetero-bispecific antibody | | | |
|---|---|---|---|---|---|
| | | PTCWT | PTC019 | PTC074 | PTC111 |
| Fc1-1 homo-dimer | 187.4 | <1 | <1 | <1 | <1 |
| Fc1-2 hetero-dimer | 136.5 | 40.6 | 68.8 | 90.4 | 89.9 |
| Fc-2-2 homo-dimer | 94.4 | 27.1 | 16.5 | <1 | <1 |
| Fc1 monomer | 77.4 | 32.3 | <1 | <1 | <1 |
| Fc 2 monomer | 41.0 | <1 | 14.6 | 5.4 | 6.0 |

Figure 8:
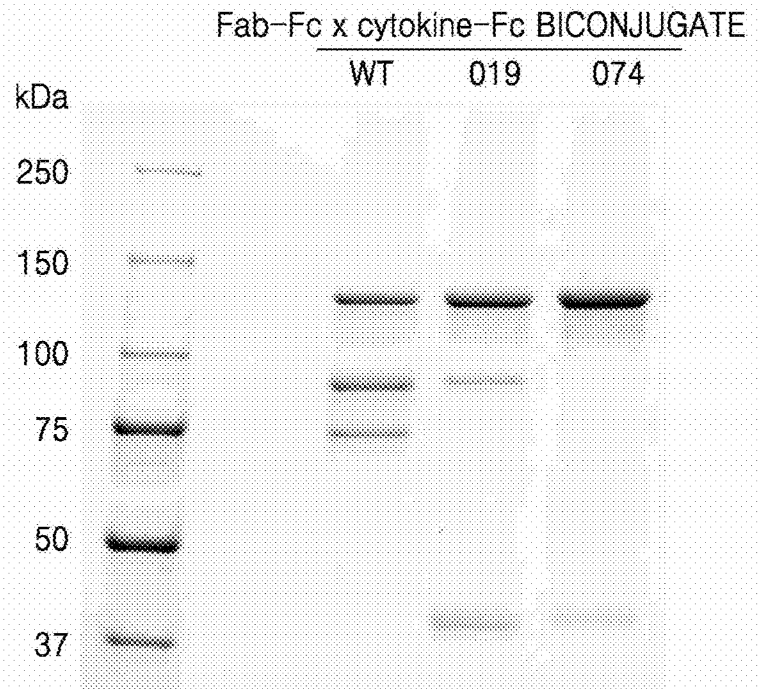
FIG. 8 is an image showing results of SDS-PAGE analysis of Fab-Fc×cytokine-Fc biconjugates (M: size marker, WT: Fab-Fc×cytokine-Fc biconjugate with a PTCWT sequence applied to a CH3 domain (negative control group), 019: Fab-Fc×cytokine-Fc biconjugate with a PTC019 sequence applied to a CH3 domain (positive control group), 074: Fab-Fc×cytokine-Fc biconjugate with a PTC074 sequence applied to a CH3 domain).

FIG. 8 is an image showing results of SDS-PAGE analysis of Fab-Fc×cytokine-Fc biconjugates (M: size marker, WT: Fab-Fc×cytokine-Fc biconjugate with a PTCWT sequence applied to the CH3 domain (negative control group), 019: Fab-Fc×cytokine-Fc biconjugate with a PTC019 sequence applied to the CH3 domain (positive control group), 074: Fab-Fc×cytokine-Fc biconjugate with a PTC074 sequence applied to the CH3 domain).

As a result, as shown in FIG. 8, it was confirmed that the Fab-Fc×cytokine-Fc biconjugate to which PTC074 and PTC111 sequences were applied had a reduced band intensity at 94.4 kDa (Fc-2-2 homo-dimer) and 77.4 kDa (Fc1 monomer), and the band intensity increased at 136.5 kDa (Fc-1-2 hetero-dimer), compared to the negative control group (PTCWT) or the positive control group (PTC019). Therefore, in the Fab-Fc×cytokine-Fc biconjugate to which PTC074 and PTC111 sequences were applied, formation of a Fc-2-2 homo-dimer band and Fc-1 monomers were reduced, and thus, it may be seen that Fc-1-2 hetero-dimers were formed with high efficiency.

In addition, as shown in Table 10, according to the structure in which sequences of the negative control group (PTCWT), positive control group (PTC019), PTC074, and PTC111 are reflected in the Fab-Fc×Cytokine-Fc biconjugate, the ratio of Fc-1-2 heterodimers was 40.6%, 68.8%, 90.4%, and 89.9%, respectively, and it was confirmed that the biconjugates reflecting PTC074 and PTC111 had a significantly higher heterodimer formation rate, compared to the negative control group (PTCWT) and the positive control group (PTC019).

That is, it may be seen that the Fc variant according to an aspect may be applied as a structure that forms an antibody, and when a cytokine protein is applied, heterodimer forming ability is excellent.

7-4. Fab-Fc×Fab-Fc Bispecific Antibody

In order to evaluate heterodimer formation rates of the hetero-bispecific antibodies including the high-efficiency Fc variants selected in Example 3, both the first polypeptide and the second polypeptide were designed to express bispecific antibodies of an intact form in which both heavy and light chains are linked. Specifically, Fc1 was expressed based on the Avelumab antibody (Bavencio, Pfizer) including the wild-type IgG1 Fc region, and Fc2 was expressed based on the bevacizumab antibody (Avastin, Roche) including the IgG1 Fc region.

For comparison, a Fab-Fc×Fab-Fc hetero-bispecific antibody including a Fc variant having the wild-type CH3 domain sequence (corresponding to "PTCWT" in Table 1) was used as a negative control group, and a Fab-Fc×Fab-Fc hetero-bispecific antibody including a Fc variant (corresponding to "PTC019" in Table 1) having Genentech's knobs-into-hole (KiH) sequence in the CH3 domain was used as a positive control group.

As an evaluation method, Intact MASS (ESI-LC-MS) analysis method was used. Specifically, liquid chromatography-mass spectrometry (LC-MS) was performed by using Thermo Scientific Dionex™ UHPLC Ultimate 3000 and TripleTOF 5600+ (AB sciex), and Analyst® software and PeakView® Software were used as analysis programs to calculate the heterodimer-forming ability, and the results are shown in Table 11 below.

TABLE 11

| Note | Measured value (m/z) | Ratio (%) CH3 domain sequence of Fab-Fc × Fab-Fc hetero-bispecific antibody | | | | |
|---|---|---|---|---|---|---|
| | | PTCWT | PTC019 | PTC039 | PTC040 | PTC074 |
| Fc1-2 hetero dimer | 147,807~148,584 | 25.4 | 32.4 | 58.1 | 40.5 | 46.8 |
| Fc1 or Fc 2 homo-dimer | 147,921~149,245 | 25.2 | 7.6 | 9.5 | 14.7 | 7.6 |

TABLE 11-continued

| Note | Measured value (m/z) | Ratio (%) CH3 domain sequence of Fab-Fc × Fab-Fc hetero-bispecific antibody PTCWT | PTC019 | PTC039 | PTC040 | PTC074 |
|---|---|---|---|---|---|---|
| Fc1 or Fc 2 monomer | 74,497~74,926 | — | 60.0 | 23.7 | 35.1 | — |
| Free light chain | 21,115~27,103 | 49.4 | — | 8.7 | 9.8 | 45.7 |

As shown in Table 11, it was confirmed that Fc-1-2 hetero-dimer formation rates of the Fab-Fc×Fab-Fc hetero-bispecific antibodies, to which sequences of the negative control group (PTCWT) and the positive control group (PTC019) were applied, were respectively 25.4% and 32.4%, on the other hand, Fc-1-2 hetero-dimer formation rates of the hetero-bispecific antibodies having a CH3 domain sequences of PTC039, PTC040, and PTC074 were 58.1%, 40.5%, and 46.8%, respectively.

That is, it may be seen that the Fc variant according to an aspect is not only easy to apply as a bispecific antibody, but also has excellent heterodimer formation when applied as the above structure.

Example 8. Evaluation of Anticancer Activity of Fab-Fc×scFv-Fc Bispecific Antibodies Including High-Efficiency Fc Variants 8-1. Confirmation of Cancer Cell Death and Inhibition of Cancer Growth The anti-PD-L1×anti-CD3 scFv bispecific antibody prepared in Example 7-1 was evaluated for its ability to kill cancer cells and inhibit cancer growth.

Specifically, 10% (v/v) FBS and 1% (v/v) penicillin-streptomycin was added to RPM11640 medium (#11875-093, Gibco), and breast cancer cells (MDA-MB-231) were cultured at 37° C. under the conditions of 5% $CO_2$. After dividing the cells in a 96-well plate at a concentration of 10,000 cells/well, the cells were cultured overnight at 37° C. under the conditions of 5% $CO_2$, and human peripheral blood mononuclear cells (PBMC) (effector cells) were co-cultured after being divided at a ratio of 20:1 (effector cells: target (MDA-MB-231) cells). Then, the cells were treated with anti-PD-L1×anti-CD3 scFv bispecific antibodies in the wells, and then cultured for 48 hours. Then, after recovering the supernatant, cytotoxicity was analyzed according to Equation 1 below by using an LDH Cytotoxicity assay kit (#C20301, Invitrogen). Avelumab (anti-PD-L1 antibody, Bavencio®) was used as a positive control group.

[Equation 1]

$$\%\ \text{Cytotoxicity} = \frac{LDH\ \text{activity when treated with compound} - \text{spontaneous}\ LDH\ \text{activity}}{\text{maximum}\ LDH\ \text{activity} - \text{spontaneous}\ LDH\ \text{activity}} \times 100\%$$

TABLE 12

| | MDA-MB-231 cancer cell growth inhibitory effect ($EC_{50}$) |
|---|---|
| Anti-PD-L1 × anti-CD3 scFv BsAb | 1.3 ng/mL |
| Avelumab (anti-PD-L1 antibody) | 11.8 ng/mL |

Figure 9:
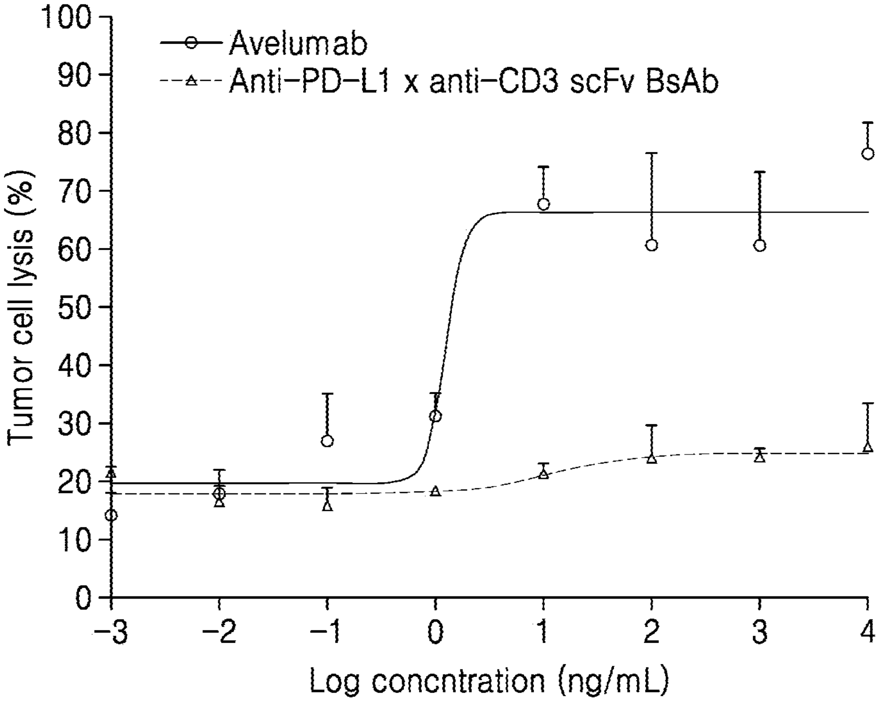
FIG. 9 is a graph evaluating the ability of anti-PD-L1× anti-CD3 scFv bispecific antibodies to induce cancer cell death in vitro (Avelumab: positive control group, anti-PD-L1×anti-CD3 scFv BsAb: anti-PD-L1×anti-CD3 scFv bispecific antibody having a PTC074 sequence in a CH3 domain).

FIG. 9 is a graph evaluating the ability of anti-PD-L1×anti-CD3 scFv bispecific antibodies to induce cancer cell death in vitro (Avelumab: positive control group, anti-PD-L1×anti-CD3 scFv BsAb: anti-PD-L1×anti-CD3 scFv bispecific antibody having a PTC074 sequence in the CH3 domain).

As a result, as shown in FIG. 9, the Emax (maximum cytotoxic effect) of the positive control group was 26% at the maximum concentration of the substance, whereas the Emax of the Fab-Fc×scFv-Fc hetero-bispecific antibody was 76.3%, and the hetero-bispecific antibody was confirmed to have remarkably high cytotoxic effect on cancer cells. In addition, the positive control group showed saturation without further increase of cell lysis at a substance concentration of $2_{log}$ ng/mL or more, and it was confirmed that an effective amount was formed in the range of $0_{log}$ ng/mL to $2_{log}$ ng/mL. On the other hand, the Fab-Fc×scFv-Fc hetero-bispecific antibody showed saturation without further increase of cell lysis at a substance concentration of 1b ng/mL or more, and it was confirmed that an effective amount was formed in the range of $-1_{log}$ ng/mL to $1_{log}$ ng/mL.

In addition, as shown in Table 12, in case of the positive control group, inhibitory effect on growth of MDA-MB-231 cancer cells was represented by $EC_{50}$ of 11.8 ng/mL, whereas the Fab-Fc×scFc-Fc hetero-bispecific antibody had $EC_{50}$ of 1.3 ng/mL, and the hetero-bispecific antibody was confirmed to be more efficient in inhibiting growth of cancer cells.

That is, the Fab-Fc×scFv-Fc hetero-bispecific antibody formed by the Fc variant according to an aspect shows an excellent anticancer effect at a lower concentration compared to known immunotherapy drugs, and side effects of existing therapeutic agents such as normal cell destruction or resistance may be reduced.

8-2. Confirmation of Anticancer Efficacy

In vivo anticancer efficacy of anti-PD-L1×anti-CD3 scFv bispecific antibody was evaluated by using a humanized mouse xenograft model. Specifically, a mixture of MDA-MB-231 cells ($5\times10^6$) and purified human T cells ($2.5\times10^6$) was mixed with the same amount of Matrigel, and subcutaneously administered to NOD/SCID mice (female, 6 weeks old, Jabio) in the flank at a dose of 0.2 mL/mouse. One hour after inoculation, 2.5 mg/kg of the anti-PD-L1×anti-CD3 scFv bispecific antibody prepared in Example 7-1 was intravenously administered (5 times/week). Avelumab, a positive control, was administered intravenously (3 times/week) at 20 mg/kg. From 7 days after inoculation, tumor volumes were measured (3 times/week) to compare and evaluate anticancer efficacies of the two substances.

Figure 10:
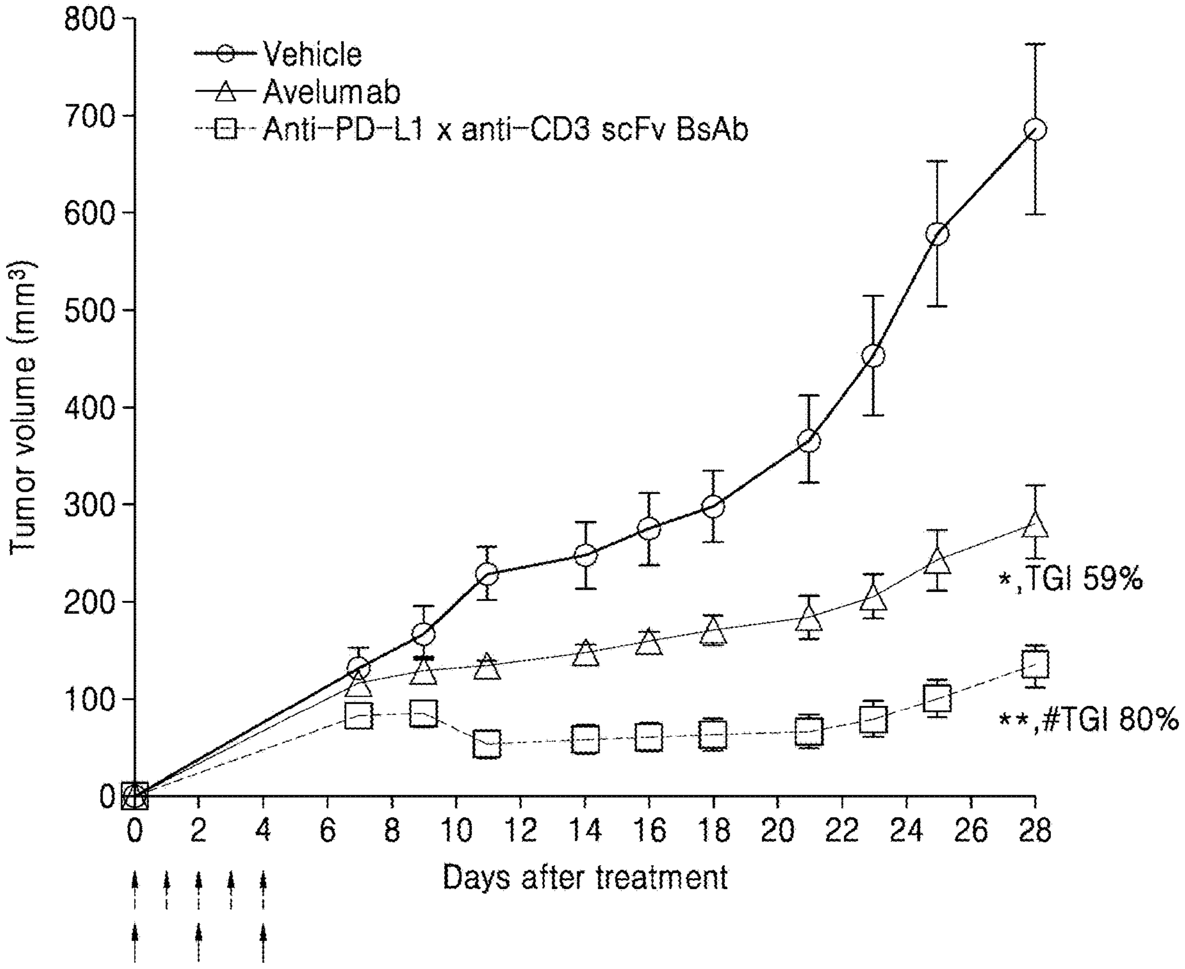
FIG. 10 is a graph evaluating the ability of anti-PD-L1× anti-CD3 scFv bispecific antibodies to inhibit cancer cell growth in vivo (Avelumab: positive control group, anti-PD-L1×anti-CD3 scFv BsAb: anti-PD-L1×anti-CD3 scFv bispecific antibody having a PTC074 sequence in a CH3 domain).

FIG. 10 is a graph evaluating the ability of anti-PD-L1×anti-CD3 scFv bispecific antibodies to inhibit cancer cell growth in vivo (Avelumab: positive control group, anti-PD-L1×anti-CD3 scFv BsAb: anti-PD-L1×anti-CD3 scFv bispecific antibody having a PTC074 sequence in the CH3 domain).

As a result, as shown in FIG. 10, in case of the negative control group, average tumor volume gradually increased for 28 days until it became 600 $mm^3$ or more, and it was confirmed that there was no tumor growth inhibitory effect. In addition, in case of the positive control group, tumor volume continued to increase, and it was confirmed that the tumor growth inhibitory effect was 59% on the day 28. On the other hand, in case of Fab-Fc×scFv-Fc, tumor growth inhibition regression was maintained the same from days 9 to 21, and the tumor growth inhibition effect was 80% on day 28, and the bispecific antibody was confirmed to effectively reduce tumor growth in humanized mouse xenograft models.

That is, the Fab-Fc×scFv-Fc hetero-bispecific antibody formed by the Fc variant according to an aspect has excellent tumor growth inhibitory effect, and thus may be used for prevention or treatment of various cancers, including breast cancer.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

The invention claimed is:

1. A protein complex comprising a first polypeptide including a first CH3 antibody constant region and a second polypeptide including a second CH3 antibody constant region, wherein the first polypeptide and the second polypeptide form a heterodimer;

wherein the first CH3 antibody constant region comprises tryptophan (W) at position 366; and wherein the second CH3 antibody constant region comprises serine(S) at position 366, alanine (A) at position 368, valine (V) at position 407, and phenylalanine (F) or glycine (G) at position 351, wherein the position of the amino acid is according to the Kabat EU index.

2. The protein complex of claim 1, comprising any one selected from the group consisting of an antigen-binding fragment (Fab), a single chain variable fragment (scFv), an extracellular domain of a membrane receptor, an agonist, an antagonist, a ligand, a decoy receptor, a cytokine, a coagulation factor, and an affinity tag.

3. A method of preparing a protein complex, comprising: transforming one or more cells with one or more expression vectors encoding the first polypeptide of claim 1, the second polypeptide of claim 1, or a combination thereof; and expressing the first polypeptide, the second polypeptide, or a combination thereof.

4. The method of claim 3, wherein the expression vector encoding the first polypeptide and the expression vector encoding the second polypeptide are co-transfected into cells, or the expression vector encoding the first polypeptide and the expression vector encoding the second polypeptide are transformed into at least two types of cells, respectively.

5. The method of claim 3, comprising: obtaining a protein complex of the first polypeptide, the second polypeptide, or the first polypeptide and the second polypeptide, from the cells or a cell culture medium.

6. The method of claim 3, wherein the protein complex comprises one selected from the group consisting of an antigen-binding fragment (Fab) thereof, a single chain variable fragment (scFv), an extracellular domain of a membrane receptor, an agonist, an antagonist, a ligand, a decoy receptor, a cytokine, a coagulation factor, and an affinity tag.

7. A method of treating cancer, comprising: administering the protein complex of claim 1 to a cell or an organism.

8. The protein complex of claim 2, wherein the Fab comprises anti-PD-L1 Fab, or anti-VEGF Fab, the scFv comprises anti-CD3 scFv, anti-VEGF scFv, and anti-CD3 scFv-anti-VEGF scFv, and the cytokine comprises IL-2 or IL-2 variant.

* * * * *

```
                          SEQUENCE LISTING


<160> NUMBER OF SEQ ID NOS: 9

<210> SEQ ID NO 1
<211> LENGTH: 450
<212> TYPE: PRT
<213> ORGANISM: Artificial
<220> FEATURE:
<223> OTHER INFORMATION: Heavy chain of Fc1 in PTCWT

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 216
<212> TYPE: PRT
<213> ORGANISM: Artificial
<220> FEATURE:
<223> OTHER INFORMATION: Light chain of Fc1 in PTCWT

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 3
<211> LENGTH: 232
<212> TYPE: PRT
<213> ORGANISM: Artificial
<220> FEATURE:
<223> OTHER INFORMATION: Fc chain of Fc2 in PTCWT

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 4
<211> LENGTH: 450
<212> TYPE: PRT
<213> ORGANISM: Artificial
<220> FEATURE:
<223> OTHER INFORMATION: Heavy chain of Fc1 in PTC019

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

-continued

```
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly Lys
450

<210> SEQ ID NO 5
<211> LENGTH: 232
<212> TYPE: PRT
<213> ORGANISM: Artificial
<220> FEATURE:
<223> OTHER INFORMATION: Fc chain of Fc2 in PTC019

<400> SEQUENCE: 5

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Ser Cys Ala Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Val
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 6
<211> LENGTH: 450
<212> TYPE: PRT
<213> ORGANISM: Artificial
<220> FEATURE:
<223> OTHER INFORMATION: Heavy chain of Fc1 in PTC039

<400> SEQUENCE: 6

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ile Met Met Trp Val Arg Gln Ala Pro Gly Lys Gly Leu Glu Trp Val
35 40 45

Ser Ser Ile Tyr Pro Ser Gly Gly Ile Thr Phe Tyr Ala Asp Thr Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Phe Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 7
```

<211> LENGTH: 232
<212> TYPE: PRT
<213> ORGANISM: Artificial
<220> FEATURE:
<223> OTHER INFORMATION: Fc chain of Fc2 in PTC039

<400> SEQUENCE: 7

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Gly Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 8
<211> LENGTH: 450
<212> TYPE: PRT
<213> ORGANISM: Artificial
<220> FEATURE:
<223> OTHER INFORMATION: Heavy chain of Fc1 in PTC040

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Trp Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 9
<211> LENGTH: 232
<212> TYPE: PRT
<213> ORGANISM: Artificial
<220> FEATURE:
<223> OTHER INFORMATION: Fc chain of Fc2 in PTC111
```

-continued

```
<400> SEQUENCE: 9

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Phe Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```